US007959933B2

(12) United States Patent
Dolly et al.

(10) Patent No.: US 7,959,933 B2
(45) Date of Patent: *Jun. 14, 2011

(54) ACTIVATABLE RECOMBINANT NEUROTOXINS

(75) Inventors: J. Oliver Dolly, Cheam (GB); Yan Li, London (GB); Kuo Chion Chan, London (GB)

(73) Assignee: Allergan, Inc., Irvine, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 12/182,801

(22) Filed: Jul. 30, 2008

(65) Prior Publication Data

US 2008/0311622 A1    Dec. 18, 2008

Related U.S. Application Data

(60) Continuation of application No. 11/326,265, filed on Jan. 5, 2006, now Pat. No. 7,419,676, which is a division of application No. 09/648,692, filed on Aug. 25, 2000, now Pat. No. 7,132,259.

(60) Provisional application No. 60/150,710, filed on Aug. 25, 1999.

(51) Int. Cl.
   *C07K 14/33*    (2006.01)
   *C12N 15/62*    (2006.01)
   *C12P 21/02*    (2006.01)

(52) U.S. Cl. ........... 424/239.1; 424/236.1; 536/23.2; 514/2; 514/12; 530/350; 435/69.1; 435/69.7; 435/252.3; 435/320.1

(58) Field of Classification Search ............ 424/239.1, 424/236.1, 9.1; 514/2, 12; 530/350; 435/252.7, 435/252.3, 69.1, 69.7, 320.1; 536/23.2
See application file for complete search history.

(56) References Cited

U.S. PATENT DOCUMENTS

| | | | |
|---|---|---|---|
| 4,683,202 A | 7/1987 | Mullis | |
| 4,800,159 A | 1/1989 | Mullis | |
| 5,919,665 A | 7/1999 | Williams | |
| 5,939,070 A | 8/1999 | Johnson et al. | |
| 5,989,545 A | 11/1999 | Foster et al. | |
| 6,395,513 B1 | 5/2002 | Foster et al. | |
| 6,461,617 B1 | 10/2002 | Shone et al. | |
| 6,632,440 B1 | 10/2003 | Quinn et al. | |
| 6,962,703 B2 | 11/2005 | Foster et al. | |
| 7,052,702 B1 | 5/2006 | Duggan et al. | |
| 7,132,259 B1 | 11/2006 | Dolly et al. | |
| 7,192,596 B2 | 3/2007 | Shone et al. | |
| 7,419,676 B2 * | 9/2008 | Dolly et al. ............. | 424/239.1 |
| 7,422,877 B2 * | 9/2008 | Dolly et al. ............. | 435/69.1 |
| 2003/0180289 A1 | 9/2003 | Foster et al. | |
| 2004/0071736 A1 | 4/2004 | Quinn et al. | |
| 2006/0024331 A1 | 2/2006 | Fernandez-Salas et al. | |
| 2006/0099672 A1 | 5/2006 | Dolly et al. | |
| 2007/0259401 A1 | 11/2007 | Dolly et al. | |
| 2008/0032930 A1 | 2/2008 | Steward et al. | |
| 2008/0032931 A1 | 2/2008 | Steward et al. | |
| 2008/0081355 A1 | 4/2008 | Dolly et al. | |
| 2008/0161226 A1 | 7/2008 | Steward et al. | |
| 2008/0161543 A1 | 7/2008 | Steward et al. | |
| 2008/0182294 A1 | 7/2008 | Dolly et al. | |

FOREIGN PATENT DOCUMENTS

| | | |
|---|---|---|
| EP | 0359347 | 3/1990 |
| WO | WO 94/21300 | 9/1994 |
| WO | WO 95/32738 | 12/1995 |
| WO | WO 96/33273 | 10/1996 |
| WO | WO 98/07864 | 2/1998 |
| WO | WO 98/08540 | 3/1998 |
| WO | WO 99/17806 | 4/1999 |
| WO | WO 99/55359 | 11/1999 |
| WO | WO01-14570 | 3/2001 |
| WO | WO2004-024909 | 3/2004 |
| WO | WO 2005/023309 | 3/2005 |
| WO | WO 2006/027207 | 3/2006 |
| WO | WO 2006/059093 | 6/2006 |
| WO | WO 2006/059105 | 6/2006 |
| WO | WO2006/059113 | 6/2006 |

OTHER PUBLICATIONS

U.S. Appl. No. 60/150,710, filed Aug. 25, 1999, Dolly et al.
U.S. Appl. No. 11/781,359, filed Jul. 23, 2007, Dolly et al.
U.S. Appl. No. 11/829,475, filed Jul. 27, 2007, Steward et al.
U.S. Appl. No. 11/832,108, filed Aug. 1, 2007, Steward et al.
U.S. Appl. No. 11/832,173, filed Aug. 1, 2007, Steward et al.
U.S. Appl. No. 11/833,142, filed Aug. 2, 2007, Steward et al.
U.S. Appl. No. 11/833,720, filed Aug. 3, 2007, Steward et al.
U.S. Appl. No. 11/834,068, filed Aug. 6, 2007, Steward et al.
U.S. Appl. No. 11/844,517, filed Aug. 24, 2007, Steward et al.
U.S. Appl. No. 11/844,546, filed Aug. 24, 2007, Steward et al.
U.S. Appl. No. 11/844,780, filed Aug. 24, 2007, Steward et al.
U.S. Appl. No. 11/844,850, filed Aug. 24, 2007, Steward et al.
U.S. Appl. No. 11/844,885, filed Aug. 24, 2007, Steward et al.
U.S. Appl. No. 11/844,899, filed Aug. 24, 2007, Steward et al.
U.S. Appl. No. 11/844,919, filed Aug. 24, 2007, Steward et al.
U.S. Appl. No. 11/844,929, filed Aug. 24, 2007, Steward et al.
U.S. Appl. No. 11/845,167, filed Aug. 27, 2007, Steward et al.
U.S. Appl. No. 11/845,185, filed Aug. 27, 2007, Dolly et al.
U.S. Appl. No. 11/845,252, filed Aug. 27, 2007, Steward et al.
U.S. Appl. No. 11/845,284, filed Aug. 27, 2007, Steward et al.
U.S. Appl. No. 11/845,320, filed Aug. 27, 2007, Steward et al.
U.S. Appl. No. 11/845,345, filed Aug. 27, 2007, Steward et al.
U.S. Appl. No. 11/845,466, filed Aug. 27, 2007, Steward et al.
U.S. Appl. No. 11/926,812, filed Oct. 29, 2007, Dolly et al.
U.S. Appl. No. 11/845,157, filed Aug. 27, 2007, Steward et al. U.S. Appl. No. 12/177,415, filed Jul. 28, 2008, Steward et al.
Borodic et al, "Pharmacology and Histology of the Therapeutic Application of Botulinum Toxin Application of Botulinum Toxins", pp. 119-157 (1994).
Tonello et al, "Tetanus and Botulinum Neurotoxins a Novel Group of Zinc-Endopeptidases", Intracellular Protein Catabolism, Adv. Exp. Med. & Biol. 389, pp. 251-260 (1996).

(Continued)

*Primary Examiner* — Chih-Min Kam
(74) *Attorney, Agent, or Firm* — Kenton Abel; Debra Condino

(57) ABSTRACT

Compositions comprising activatable recombinant neurotoxins and polypeptides derived therefrom. The invention also comprises nucleic acids encoding such polypeptides, and methods of making such polypeptides and nucleic acids.

12 Claims, 18 Drawing Sheets

OTHER PUBLICATIONS

Li, Yan et al., "A Single Mutation in the Recombinant Light Chain of Tetanus Toxin Abolishes Its Proteolytic Activity and Removes the Toxicity Seen After Reconstitution with Native Heavy Chain", Biochemistry (1994), 33(22), 7014-20 CODEN: Bichaw; Issn: 0006-2960: pp. 7014-7020.

Coffield et al., "The Site and Mechanism of Action of Botulinum Neurotoxin", Neurological Disease and Therapy, pp. 3-13, 25 (Jankovic J. & Hallett M. eds. 1994).

Foran et al, "Botulinum Neurotoxin Cl Cleaves both Syntaxin and SNAP-25 in Intact and Permeabilized Chromaffin Cells: Correlation with Its Blockade of Catecholamine Release", Biochem. 35: pp. 2630-2636 (1996).

Dolly et al, "Probing the process of transmitter release with botulinum and tetanus neurotoxins" Seminars in Neuroscience, 6(3): pp. 149-158 (1994).

Zhou et al, "Expression and Purification of the Light Chain of Botulinum Neurotoxin A: A Single Mutation Abolishes Its Cleavage of SNAP-25 and Neurotoxiicity after Reconstruction with the Heavy Chain", Biochemistry 34: pp. 15175-15181 (1995).

Lacy et al, "Crystal structure of botulinum neurotoxin type A and implications for toxicity" Nature Struct. Biol. Oct; 5 (10): pp. 898-902 (1998).

Kurazono et al, "Minimal Essential Domains Specifying Toxicity of the Light Cahins of Tetanus Toxin and Botulinum Neurotoxin Type A", J. Biol. Chem.: pp. 14721-14729 (1992).

Smith et al, "Mutagenesis at a Specific Position in a DNA Sequence", J. Biol. Chem. 253: No. 18, Sep. 25 issue, pp. 6651-6560 (1978).

Li et al, "Expression and Characterization of the Heavy Chain of Tetanus Toxin: Reconstruction of the Fully-Recombinant Dichain Proetin in Active Form", J. Biochem. 125: pp. 1200-1208 (1999).

Herreros et al, "C-Terminal Half of Tetanus Toxin Fragment C is Sufficient for Neuronal Binding and Interaction with a Putative Protein Receptor", Biochemical Journal, vol. 347, No. Part 1, pp. 199-204, Apr. 1, 2001.

Rummel et al, "The Hcc-domain of botulinum neurotoxins A and B exhibits a singular ganglioside binding site displaying serotype specific carbohydrate interation", Molecular Microbiology, pp. 631-643, Dec. 15, 2003.

Halpern et al, "Characterization of the receptor-binding domain of tetanus toxin", Journal of Biological Chemistry, pp. 11188-11192, May 25, 1993.

* cited by examiner

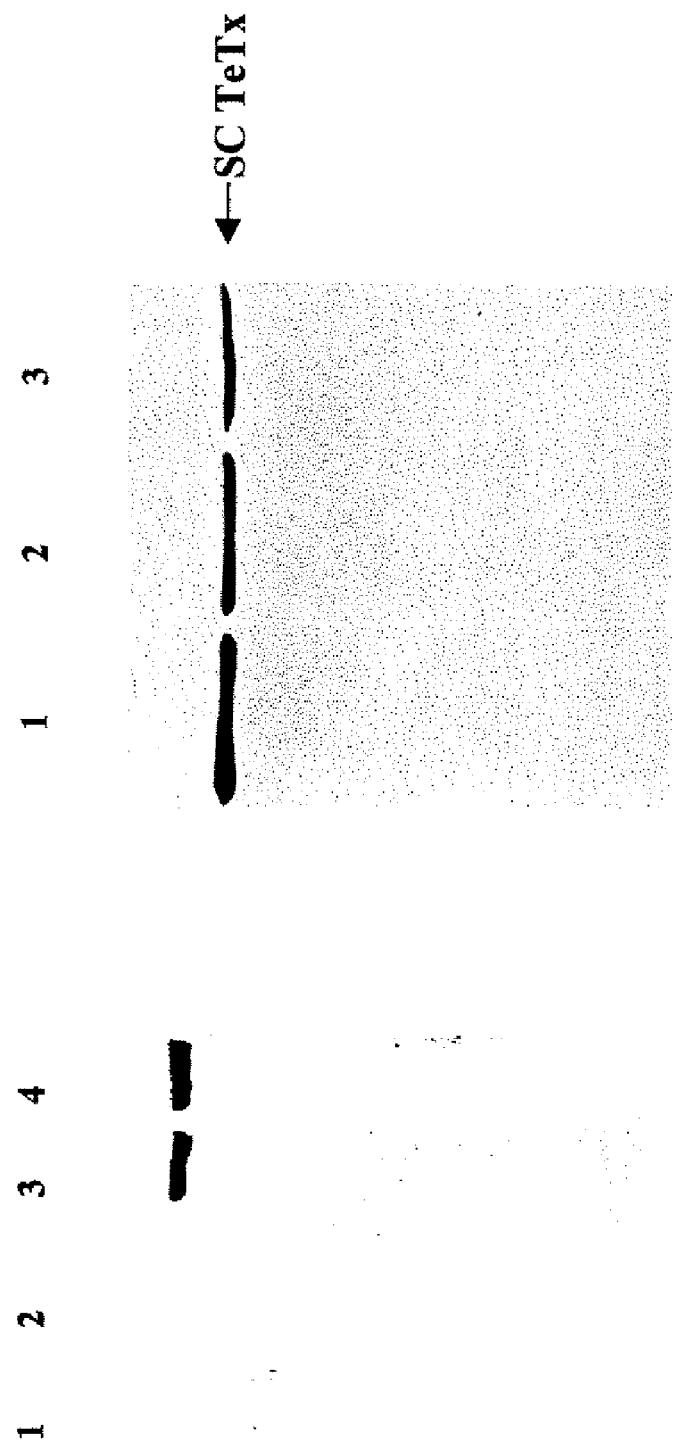

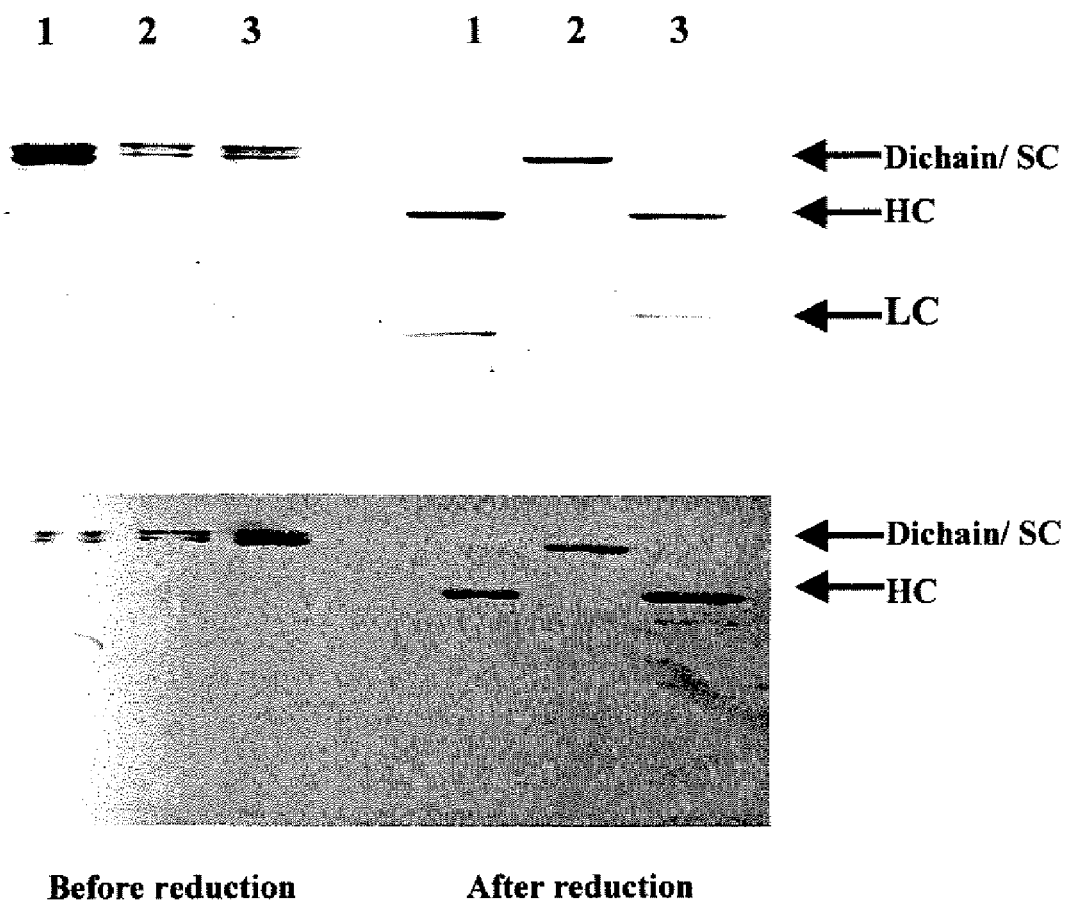

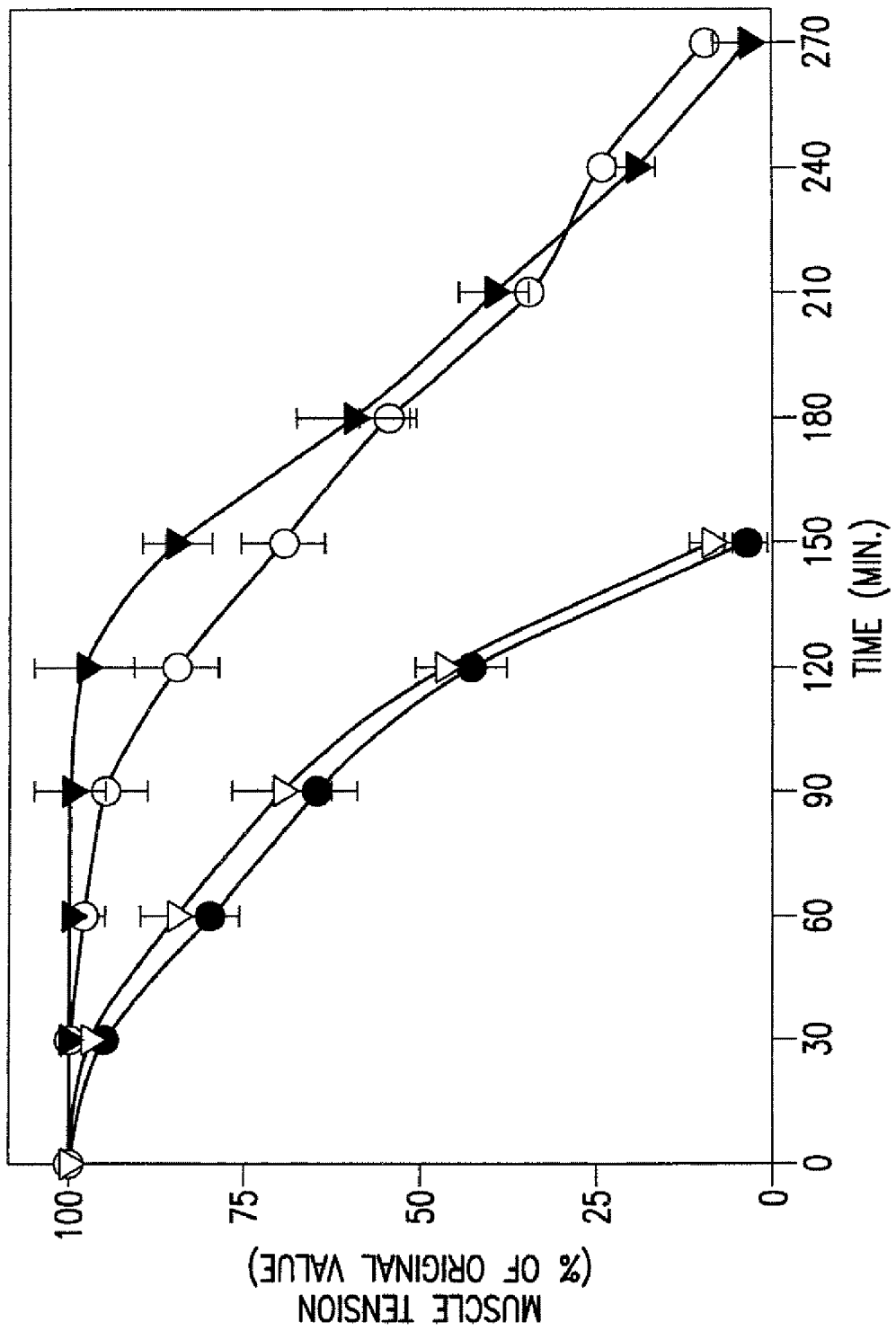

←SC TeTx WT

HC → Stained with Ponceau red
↓
HC band cut from the gel
↓
N-terminal sequencing
↓

←LC

No enzyme | Arg-C | Trypsin

GEKLYDDDDKDRWGSSR⁴⁹⁶  ⁴⁹⁷SLTDLGGELCIKIKNEDLT →

Linker sequence         HC
            ↑
Arg-C and trypsin cleavage site

FIG. 5

NICKED MUTANT

K+-EVOKED Ca²⁺-DEP. RELEASE OF [¹⁴C] GLUTAMATE/5 MIN. (% TOXIN-FREE CONTROL)

| NATIVE TeTx (0.2 nM) | − | + | + | + | + |
|---|---|---|---|---|---|
| PRE-INCUBATED WITH MUTANT TeTx (nM) | 52 | 0 | 10 | 30 | 60 |

FIG.7A

SINGLE-CHAIN MUTANT

K+-EVOKED Ca²⁺-DEP. RELEASE OF [¹⁴C] GLUTAMATE/5 MIN. (% TOXIN-FREE CONTROL)

| NATIVE TeTx (0.2 nM) | + | + | + | + |
|---|---|---|---|---|
| PRE-INCUBATED WITH MUTANT TeTx (nM) | 0 | 7 | 20 | 40 |

*CLOSTRIDIUM BOTULINUM* TYPE E (STRAIN BELUGA) CHROMOSOMAL DNA

↓ PCR WITH A PROOF READING THERMOPOLYMERASE 1 2 3

1: MARKERS
2: NEGATIVE CONTROL
3: SAMPLE

↓ 3.5-kB DNA FRAGMENT PURIFIED AND CLONED INTO BamHI AND PstI SITES OF pQE30 EXPRESSION VECTOR

| HIS TAG | BoNT/E | PstI |

BamHI

| ATG | AGA | GGA | TCG | CAT | CAC | CAT | CAC | CAT | CAC | GGA | TCC | CCA | AAA | ATT | AAT | AGT | TTT |
| M | R | G | S | H | H | H | H | H | H | G | S | P | K | I | N | S | T |
| START | | | | POLY HISTIDINE TAG | | | | | | Bam HI | | BoNT/E LIGHT CHAIN | | | | | |

CULTURE OF E.COLI M15[pQEESCwt]
↓
OVERNIGHT INDUCTION WITH IPTG
↓
HARVEST, EXTRACTION AND CENTRIFUGATION
↓
METAL CHELATE AFFINITY CHROMATOGRAPHY

SDS-PAGE (REDUCING COND.)

1: CELL-FREE EXTRACT
2: FLOW-THROUGH
3: WASH
4: ELUATE
(0.15M IMIDAZOLE)

PROTEIN STAINED

WESTERN BLOTTED
WITH ANTI-HIS IgG

← 150 kDa BoNT SC

YIELD: 0.2mg/L OF CULTURE

SEQUENCE LISTING

<160> NUMBER OF SEQ ID NOS: 30

<210> SEQ ID NO 1
<211> LENGTH: 44
<212> TYPE: DNA
<213> ORGANISM: Artificial Sequence
<220> FEATURE:
<223> OTHER INFORMATION: PCR primer

<400> SEQUENCE: 1
gactggtgga cagcaagtcg accggaagct ttacgacgat gacg                44

-continued

```
<210> SEQ ID NO 2
<211> LENGTH: 44
<212> TYPE: DNA
<213> ORGANISM: Artificial Sequence
<220> FEATURE:
<223> OTHER INFORMATION: PCR primer

<400> SEQUENCE: 2
cgtcatcgtc gtaaagcttc cggtcgactt gctgtccacc agtc            44

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
aatagatcta gatcattaac agatttagga                            30

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
ttctaaagat ctatacattt gataact                               27

<210> SEQ ID NO 5
<211> LENGTH: 27
<212> TYPE: DNA
<213> ORGANISM: Artificial Sequence
<220> FEATURE:
<223> OTHER INFORMATION: PCR primer

<400> SEQUENCE: 5
atgtatagat ctttagaata tcaagta                               27

<210> SEQ ID NO 6
<211> LENGTH: 45
<212> TYPE: DNA
<213> ORGANISM: Artificial Sequence
<220> FEATURE:
<223> OTHER INFORMATION: PCR primer

<400> SEQUENCE: 6
atcgataagc ttttatcagt cgacccaaca atccagattt ttaga           45

<210> SEQ ID NO 7
<211> LENGTH: 65
<212> TYPE: PRT
<213> ORGANISM: Artificial Sequence
<220> FEATURE:
<223> OTHER INFORMATION: Engineered Intrachain loop region for C. tetani
      toxin

<400> SEQUENCE: 7

Ser Lys Leu Ile Gly Leu Cys Lys Lys Ile Ile Pro Pro Thr Asn Ile
 1               5                  10                  15

Arg Glu Asn Leu Tyr Asn Arg Thr Ala Gly Glu Lys Leu Tyr Asp Asp
             20                  25                  30

Asp Asp Lys Asp Arg Trp Gly Ser Ser Arg Ser Leu Thr Asp Leu Gly
         35                  40                  45

Gly Glu Leu Cys Ile Lys Asn Glu Asp Leu Thr Phe Ile Ala Glu Lys
```

Asn
65

<210> SEQ ID NO 8
<211> LENGTH: 36
<212> TYPE: DNA
<213> ORGANISM: Artificial Sequence
<220> FEATURE:
<223> OTHER INFORMATION: PCR Primer

<400> SEQUENCE: 8
aatagaactg caggagaaaa gctttacgac gatgac                36

<210> SEQ ID NO 9
<211> LENGTH: 36
<212> TYPE: DNA
<213> ORGANISM: Artificial Sequence
<220> FEATURE:
<223> OTHER INFORMATION: PCR Primer

<400> SEQUENCE: 9
gtcatcgtcg taaagctttt ctcctgcagt tctatt                36

<210> SEQ ID NO 10
<211> LENGTH: 4017
<212> TYPE: DNA
<213> ORGANISM: Clostridium botulinum

<400> SEQUENCE: 10
gaattcaagt agtagataat aaaaataatg ccacagattt ttattattaa taatgatata      60
tttatctcta actgtttaac tttaacttat aacaatgtaa atatatattt gtctataaaa     120
aatcaagatt acaattgggt tatatgtgat cttaatcatg atataccaaa aaagtcatat     180
ctatggatat taaaaaatat ataaatttaa aattaggaga tgctgtatat gccaaaaatt     240
aatagtttta attataatga tcctgttaat gatagaacaa ttttatatat taaaccaggc     300
ggttgtcaag aattttataa atcatttaat attatgaaaa atatttggat aattccagag     360
agaaatgtaa ttggtacaac cccccaagat tttcatccgc ctacttcatt aaaaaatgga     420
gatagtagtt attatgaccc taattattta caaagtgatg aagaaaagga tagatttta     480
aaaatagtca caaaatatatt taatagaata aataataatc tttcaggagg gatttatta     540
gaagaactgt caaaagctaa tccatattta gggaatgata atactccaga taatcaattc     600
catattggtg atgcatcagc agttgagatt aaattctcaa atggtagcca agacatacta     660
ttacctaatg ttattataat gggagcagag cctgatttat ttgaaactaa cagttccaat     720
atttctctaa gaataatta tatgccaagc aatcaccgtt ttggatcaat agctatagta     780
acattctcac ctgaatattc tttttagattt aatgataatt gtatgaatga atttattcaa     840
gatcctgctc ttacattaat gcatgaatta atacattcat tacatggact atatgggct     900
aaagggatta ctacaaagta tactataaca caaaaacaaa atcccctaat aacaaatata     960
agaggtacaa atattgaaga attcttaact tttggaggta ctgatttaaa cattattact    1020
agtgctcagt ccaatgatat ctatactaat cttctagctg attataaaaa aatagcgtct    1080
aaacttagca agtacaagt atctaatcca ctacttaatc cttataaaga tgtttttgaa    1140
gcaaagtatg gattagataa agatgctagc ggaatttatt cggtaaatat aaacaaattt    1200
aatgatattt taaaaaatt atacagcttt acgaatttg attacgaac taaatttcaa    1260
gttaaatgta ggcaaactta tattggacag tataaatact caaactttc aaacttgtta    1320

```
aatgattcta tttataatat atcagaaggc tataatataa ataatttaaa ggtaaatttt  1380
agaggacaga atgcaaattt aaatcctaga attattacac caattacagg tagaggacta  1440
gtaaaaaaaa tcattagatt ttgtaaaaat attgtttctg taaaaggcat aaggaaatca  1500
atatgtatcg aaataaataa tggtgagtta ttttttgtgg cttccgagaa tagttataat  1560
gatgataata taaatactcc taaagaaatt gacgatacag taacttcaaa taataattat  1620
gaaaatgatt tagatcaggt tattttaaat tttaatagtg aatcagcacc tggactttca  1680
gatgaaaaat taaatttaac tatccaaaat gatgcttata taccaaaata tgattctaat  1740
ggaacaagtg atatagaaca acatgatgtt aatgaactta atgtattttt ctatttagat  1800
gcacagaaag tgcccgaagg tgaaaataat gtcaatctca cctcttcaat tgatacagca  1860
ttattagaac aacctaaaat atatacattt ttttcatcag aatttattaa taatgtcaat  1920
aaacctgtgc aagcagcatt atttgtaagc tggatacaac aagtgttagt agattttact  1980
actgaagcta accaaaaaag tactgttgat aaaattgcag atatttctat agttgttcca  2040
tatataggtc ttgctttaaa tataggaaat gaagcacaaa aaggaaattt taaagatgca  2100
cttgaattat taggagcagg tattttatta gaatttgaac ccgagctttt aattcctaca  2160
attttagtat tcacgataaa atctttttta ggttcatctg ataataaaaa taaagttatt  2220
aaagcaataa ataatgcatt gaaagaaaga gatgaaaaat ggaaagaagt atatagttttt  2280
atagtatcga attggatgac taaaattaat acacaattta ataaaagaaa agaacaaatg  2340
tatcaagctt tacaaaatca gtaaatgca attaaaacaa taatagaatc taagtataat  2400
agttatactt tagaggaaaa aaatgagctt acaaataaat atgatattaa gcaaatagaa  2460
aatgaactta atcaaaaggt ttctatagca atgaataata tagacaggtt cttaactgaa  2520
agttctatat cctatttaat gaaaataata aatgaagtaa aaattaataa attaagagaa  2580
tatgatgaga atgtcaaaac gtattttattg aattatatta tacaacatgg atcaatcttg  2640
ggagagagtc agcaagaact aaattctatg gtaactgata ccctaaataa tagtattcct  2700
tttaagcttt cttcttatac agatgataaa attttaattt catattttaa taaattcttt  2760
aagagaatta aaagtagttc agttttaaat atgagatata aaaatgataa atacgtagat  2820
acttcaggat atgattcaaa tataaatatt aatggagatg tatataaata tccaactaat  2880
aaaaatcaat ttggaatata taatgataaa cttagtgaag ttaatatatc tcaaaatgat  2940
tacattatat atgataataa atataaaaat tttagtatta gttttgggt aagaattcct  3000
aactatgata ataagatagt aaatgttaat aatgaataca ctataataaa ttgtatgaga  3060
gataataatt caggatggaa agtatctctt aatcataatg aaataatttg gacattcgaa  3120
gataatcgag gaattaatca aaaattagca tttaactatg gtaacgcaaa tggtatttct  3180
gattatataa ataagtggat ttttgtaact ataactaatg atagattagg agattctaaa  3240
ctttatatta atgggaaattt aatagatcaa aaatcaattt taaatttagg taatattcat  3300
gttagtgaca atatattatt taaaatagtt aattgtagtt atacaagata tattggtatt  3360
agatatttta atatttttga taagaattaa gatgaaacag aaattcaaac tttatatagc  3420
aatgaaccta atacaaatat tttgaaggat ttttggggaa attatttgct ttatgacaaa  3480
gaatactatt tattaaatgt gttaaaacca aataacttta ttgataggag aaaagattct  3540
actttaagca ttaataatat aagaagcact attcttttag ctaatagatt atatagtgga  3600
ataaaagtta aaatacaaag agttaataat agtagtacta acgataatct tgttagaaag  3660
aatgatcagg tatatattaa ttttgtagcc agcaaaactc acttatttcc attatatgct  3720
```

-continued

```
gatacagcta ccacaaataa agagaaaaca ataaaaatat catcatctgg caatagattt    3780
aatcaagtag tagttatgaa ttcagtagga aattgtacaa tgaattttaa aaataataat    3840
ggaaataata ttgggttgtt aggtttcaag gcagatactg tcgttgctag tacttggtat    3900
tatacacata tgagagatca tacaaacagc aatggatgtt tttggaactt tatttctgaa    3960
gaacatggat ggcaagaaaa ataaaaatta gattaaacgg ctaaagtcat aaattcc      4017
```

```
<210> SEQ ID NO 11
<211> LENGTH: 37
<212> TYPE: DNA
<213> ORGANISM: Artificial Sequence
<220> FEATURE:
<223> OTHER INFORMATION: PCR Primer

<400> SEQUENCE: 11
cccggatccc caaaaattaa tagttttaat tataatg                             37

<210> SEQ ID NO 12
<211> LENGTH: 36
<212> TYPE: DNA
<213> ORGANISM: Artificial Sequence
<220> FEATURE:
<223> OTHER INFORMATION: PCR Primer

<400> SEQUENCE: 12
cccctgcagt cattttctct gccatccatg ttcttc                              36

<210> SEQ ID NO 13
<211> LENGTH: 31
<212> TYPE: DNA
<213> ORGANISM: Artificial Sequence
<220> FEATURE:
<223> OTHER INFORMATION: PCR Primer

<400> SEQUENCE: 13
cagttaatac attcattaca tggactatat g                                   31

<210> SEQ ID NO 14
<211> LENGTH: 26
<212> TYPE: DNA
<213> ORGANISM: Artificial Sequence
<220> FEATURE:
<223> OTHER INFORMATION: PCR Primer

<400> SEQUENCE: 14
atgcattaat gtaagagcag gatctt                                         26

<210> SEQ ID NO 15
<211> LENGTH: 5
<212> TYPE: PRT
<213> ORGANISM: Artificial Sequence
<220> FEATURE:
<223> OTHER INFORMATION: Protease cleavage site

<400> SEQUENCE: 15

Asp Asp Asp Asp Lys
 1               5

<210> SEQ ID NO 16
<211> LENGTH: 8
<212> TYPE: PRT
<213> ORGANISM: Artificial Sequence
<220> FEATURE:
<223> OTHER INFORMATION: Protease cleavage site
```

```
<400> SEQUENCE: 16

Leu Glu Val Leu Phe Gln Gly Pro
1               5

<210> SEQ ID NO 17
<211> LENGTH: 5
<212> TYPE: PRT
<213> ORGANISM: Clostridium species
<220> FEATURE:
<221> NAME/KEY: ZN_FING
<222> LOCATION: (1)...(5)
<223> OTHER INFORMATION: Zinc finger
<221> NAME/KEY: SITE
<222> LOCATION: (3)...(4)
<223> OTHER INFORMATION: Xaa=any amino acid

<400> SEQUENCE: 17

His Glu Xaa Xaa His
1               5

<210> SEQ ID NO 18
<211> LENGTH: 51
<212> TYPE: DNA
<213> ORGANISM: Artificial Sequence
<220> FEATURE:
<223> OTHER INFORMATION: Linker

<400> SEQUENCE: 18
ggagaaaagc tttacgacga tgacgataag gatcgatggg gatcctctag a           51

<210> SEQ ID NO 19
<211> LENGTH: 22
<212> TYPE: PRT
<213> ORGANISM: Artificial Sequence
<220> FEATURE:
<223> OTHER INFORMATION: Linker

<400> SEQUENCE: 19

Met Gly Gly Ser His His His His His Gly Met Ala Ser Met Thr
1               5                   10                  15

Gly Gly Gln Gln Val Asp
            20

<210> SEQ ID NO 20
<211> LENGTH: 19
<212> TYPE: PRT
<213> ORGANISM: Clostridium botulinum

<400> SEQUENCE: 20

Ser Leu Thr Asp Leu Gly Gly Glu Leu Cys Ile Lys Ile Lys Asn Glu
1               5                   10                  15

Asp Leu Thr

<210> SEQ ID NO 21
<211> LENGTH: 54
<212> TYPE: DNA
<213> ORGANISM: Artificial Sequence
<220> FEATURE:
<223> OTHER INFORMATION: Linker

<400> SEQUENCE: 21
atgagaggat cgcatcacca tcaccatcac ggatccccaa aaattaatag tttt         54

<210> SEQ ID NO 22
<211> LENGTH: 7
<212> TYPE: PRT
```

```
<213> ORGANISM: Artificial Sequence
<220> FEATURE:
<223> OTHER INFORMATION: Protease cleavage site
<221> NAME/KEY: SITE
<222> LOCATION: (2)...(3)
<223> OTHER INFORMATION: Xaa=any amino acid

<400> SEQUENCE: 22

Glu Xaa Xaa Tyr Ser Gln Ser
 1               5

<210> SEQ ID NO 23
<211> LENGTH: 7
<212> TYPE: PRT
<213> ORGANISM: Artificial Sequence
<220> FEATURE:
<223> OTHER INFORMATION: Protease cleavage site
<221> NAME/KEY: SITE
<222> LOCATION: (2)...(3)
<223> OTHER INFORMATION: Xaa=any amino acid
<221> NAME/KEY: SITE
<222> LOCATION: (5)...(5)
<223> OTHER INFORMATION: Xaa=any amino acid

<400> SEQUENCE: 23

Glu Xaa Xaa Tyr Xaa Gln Gly
 1               5

<210> SEQ ID NO 24
<211> LENGTH: 18
<212> TYPE: PRT
<213> ORGANISM: Artificial Sequence
<220> FEATURE:
<223> OTHER INFORMATION: Translated PCR fragment

<400> SEQUENCE: 24

Met Arg Gly Ser His His His His His His Gly Ser Pro Lys Ile Asn
 1               5                   10                  15

Ser Thr

<210> SEQ ID NO 25
<211> LENGTH: 5
<212> TYPE: PRT
<213> ORGANISM: Clostridium species
<220> FEATURE:
<221> NAME/KEY: ZN_FING
<222> LOCATION: (1)...(5)
<223> OTHER INFORMATION: Zinc finger

<400> SEQUENCE: 25

His Glu Leu Ile His
 1               5

<210> SEQ ID NO 26
<211> LENGTH: 5
<212> TYPE: PRT
<213> ORGANISM: Clostridium botulinum C
<220> FEATURE:
<221> NAME/KEY: ZN_FING
<222> LOCATION: (1)...(5)
<223> OTHER INFORMATION: Zinc finger

<400> SEQUENCE: 26

His Glu Leu Asn His
 1               5

<210> SEQ ID NO 27
<211> LENGTH: 5
<212> TYPE: PRT
```

```
<213> ORGANISM: Clostridium botulinum D
<220> FEATURE:
<221> NAME/KEY: ZN_FING
<222> LOCATION: (1)...(5)
<223> OTHER INFORMATION: Zinc finger

<400> SEQUENCE: 27

His Glu Leu Thr His
1               5

<210> SEQ ID NO 28
<211> LENGTH: 4
<212> TYPE: PRT
<213> ORGANISM: Homo sapiens
<220> FEATURE:
<221> NAME/KEY: SITE
<222> LOCATION: (1)...(4)
<223> OTHER INFORMATION: Blood coagulation factor Xa

<400> SEQUENCE: 28

Ile Glu Gly Arg
1

<210> SEQ ID NO 29
<211> LENGTH: 17
<212> TYPE: PRT
<213> ORGANISM: Artificial Sequence
<220> FEATURE:
<223> OTHER INFORMATION: Linker

<400> SEQUENCE: 29

Gly Glu Lys Leu Tyr Asp Asp Asp Asp Lys Asp Arg Trp Gly Ser Ser
1               5                   10                  15

Arg

<210> SEQ ID NO 30
<211> LENGTH: 5
<212> TYPE: PRT
<213> ORGANISM: Artificial Sequence
<220> FEATURE:
<223> OTHER INFORMATION: Linker

<400> SEQUENCE: 30

Ser Leu Thr Asp Leu
1               5
```

ACTIVATABLE RECOMBINANT NEUROTOXINS

This application is a continuation and claims priority pursuant to 35 U.S.C. §120 to U.S. patent application Ser. No. 11/326,265, filed Jan. 5, 2006, now U.S. Pat. No. 7,419,676, a divisional that claims priority pursuant to 35 U.S.C. §120 to U.S. patent application Ser. No. 09/648,692, filed Aug. 25, 2000, now U.S. Pat. No. 7,132,259, an application that claims priority pursuant to 35 U.S.C. §119(e) to provisional application Ser. No. 60/150,710, filed Aug. 25, 1999, which are hereby incorporated by reference in their entirety.

FIELD OF THE INVENTION

This invention concerns methods and compositions useful in the fields of neurobiology, molecular biology, and medicine, as well as methods for the production of potentially toxic therapeutic agents and derivatives thereof. The invention also concerns recombinant clostridial neurotoxins (particular botulinum neurotoxins), modified versions thereof, and methods of making such molecules, for use as therapeutic agents, transporter molecules, adducts, and the like.

BACKGROUND OF THE INVENTION

Neurotoxins, such as those obtained from *Clostridium botulinum* and *Clostridium tetani*, are highly potent and specific poisons of neural cells, and other cells when delivered within such cells for therapeutic purposes. These Gram positive bacteria express two related but distinct toxins types, each comprising two disulfide-linked amino acid chains: a light chain (L) of about 50 KDa and a heavy chain (H) of about 100 KDa, which are wholly responsible for the symptoms of these diseases. The holotoxin is synthesised in vivo as a single chain, then nicked in a post-translational modification to form the active neurotoxin comprising the separate L and H chains.

The tetanus and botulinum toxins are among the most lethal substances known to man, having a lethal dose in humans of between 0.1 ng and 1 ng per kilogram of body weight. Tonello et al., *Adv. Exp. Med. & Biol.* 389:251-260 (1996). Both toxins function by inhibiting neurotransmitter release in affected neurons. The tetanus neurotoxin (TeTx) acts mainly in the central nervous system, while botulinum neurotoxin (BoNT) acts at the neuromuscular junction and other cholinergic synapses in the peripheral nervous system; both act by inhibiting neurotransmitter release from the axon of the affected neuron into the synapse, resulting in paralysis.

The tetanus neurotoxin (TeTx) is known to exist in one immunologically distinct type; the botulinum neurotoxins (BoNT) are known to occur in seven different immunogenic types, termed BoNT/A through BoNT/G. While all of these types are produced by isolates of *C. botulinum*, two other species, *C. baratii* and *C. butyricum* also produce toxins similar to /F and /E, respectively. See e.g., Coffield et al., *The Site and Mechanism of Action of Botulinum Neurotoxin in Therapy with Botulinum Toxin* 3-13(Jankovic J. & Hallett M. eds. 1994), the disclosure of which is incorporated herein by reference.

Regardless of type, the molecular mechanism of intoxication appears to be similar. In the first step of the process, the toxin binds to the presynaptic membrane of the target neuron through a specific interaction between the heavy (H) chain and a cell surface receptor; the receptor is thought to be different for each type of botulinum toxin and for TeTx. Dolly et al., *Seminars in Neuroscience* 6:149-158 (1994), incorporated by reference herein. The carboxyl terminus of the heavy chain appears to be important for targeting of the toxin to the cell surface. Id.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino terminus of the H chain, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and light (L) chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. TeTx, BoNT/B BoNT/D, BoNT/F, and BoNT/G cause degradation of synaptobrevin (also called vesicle-associated membrane protein (VAMP)), a synaptosomal membrane protein. Most of the cytosolic domain of VAMP extending from the surface of the synaptic vesicle is removed as a result of any one of these cleavage events. Each toxin (except TeTx and BoNT/B) specifically cleaves a different bond.

BoNT/A and /E selectively cleave the plasma membrane-associated protein SNAP-25; this protein, which is also cleaved by BoNT/C1 (Foran et al., *Biochem.* 35:2630-2636 (1996)), is predominantly bound to and present on the cytosolic surface of the plasma membrane. BoNT/C cleaves syntaxin, an integral protein having most of its mass exposed to the cytosol. Syntaxin interacts with the calcium channels at presynaptic terminal active zones. See Tonello et al., *Tetanus and Botulinum Neurotoxins in Intracellular Protein Catabolism* 251-260 (Suzuki K. & Bond J. eds. 1996), the disclosure of which is incorporated by reference as part of this specification.

Both TeTx and BoNT are taken up at the neuromuscular junction. BoNT remains within peripheral neurons, and blocks release of the neurotransmitter acetylcholine from these cells. Through its receptor, TeTx enters vesicles that move in a retrograde manner along the axon to the soma, and is discharged into the intersynaptic space between motor neurons and the inhibitory neurons of the spinal cord. At this point, TeTx binds receptors of the inhibitory neurons, is again internalized, and the light chain enters the cytosol to block the release of the inhibitory neurotransmitters 4-aminobutyric acid(GABA) and glycine from these cells.

Because of its specifically localized effects, minute doses of BoNT have been used since 1981 as therapeutic agents in the treatment of patients suffering from dystonias, including strabismus (misalignment of the eye), bephlarospasm (involuntary eyelid closure) and hemifacial spasm. See e.g., Borodic et al, *Pharmacology and Histology of the Therapeutic Application of Botulinum Toxin in Therapy with Botulinum Toxin* 119-157 (Jankovic J. & Hallett eds. 1994), hereby incorporated by reference herein. Of the seven toxin types, BoNT/A is the most potent of the BoNTs, and the best characterized. Intramuscular injection of spastic tissue with small quantities of BoNT/A has also been used effectively to treat spasticity due to brain injury, spinal cord injury, stroke, multiple sclerosis and cerebral palsy. The extent of paralysis depends on both the dose and volume delivered to the target site.

Although the L chain is the moiety responsible for neural intoxication, it must be delivered to the neural cytoplasm in order to be toxic. Similarly, the single chain holotoxin proforms exhibit relatively low toxicity until they are cleaved at one or more peptide bonds in an exposed loop region between their H and L chains to create the fully-active mature neurotoxins. As implied in the mechanism provided above, the H chain of each neurotoxin is essential for cell receptor binding and endocytosis, while both the L and the H chains (and an intact disufide bond) are required for translocation of the toxin into the cytoplasm. As indicated above, the L chain alone is responsible for the toxicity caused by inhibition of acetylcholine secretion.

Despite the clear therapeutic efficacy of clostridial neurotoxin preparations, industrial production of the toxin is difficult. Production of neurotoxin from anaerobic *Clostridium* cultures is a cumbersome and time-consuming process including a multi-step purification protocol involving several protein precipitation steps and either prolonged and repeated crystallisation of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking. This involves the removal of approximately 10 amino acid residues from the single-chain to create the dichain form in which the two chains remain covalently linked through the interchain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *C. botulinum* type A single-chain neurotoxin is activated by the Hall A *C. botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as BoNT and TeTx could be expressed in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of TeTx and BONT; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L subunits can be combined by oxidative disulphide linkage to form the neuroparalytic di-chains. Unfortunately, this strategy has several drawbacks.

Firstly, it is not practical to express and isolate large amounts of the individual chains; in particular, in the absence of the L chain the isolated H chain is quite insoluble in aqueous solution and is highly susceptible to proteolytic degradation. Secondly, the in vitro oxidation of the individually expressed and purified H and L chains to produce the active di-chain is very inefficient, and leads to low yields of active toxin and the production of many inactive incorrectly folded or oxidized forms. The purification of the correctly folded and oxidized H and L chain-containing toxin is difficult, as is its separation from these inactive forms and the unreacted separate H and L chains.

It would therefore be useful and advantageous to express clostridial neurotoxins as inactive (or less active) single-chain forms, to eliminate the need for the time-consuming and inefficient reconstitution of the constituent chains, to maintain solubility of the protein chains, to reduce protein misfolding and consequent susceptibility to protease attack, to improve toxin yield, and/or to provide a simple method for the purification of the toxin.

Additionally, it would be useful to engineer these toxins to provide single-chain, modified neurotoxin molecules having novel therapeutic properties and/or longer duration of action, or toxic or non-toxic forms for use as transport molecules capable of delivering a therapeutic moiety to nerve or other cell types. By expressing such proteins as a single chain, the yield and purification of the engineered proteins would be vastly improved.

SUMMARY OF THE INVENTION

The present invention is directed to recombinant and isolated proteins comprising a functional binding domain, translocation domain, and therapeutic domain in which such proteins also include an amino acid sequence that is susceptible to specific cleavage in vitro following expression as a single chain. Such proteins may include clostridial neurotoxins and derivatives thereof, such as those proteins disclosed in U.S. Pat. No. 5,989,545 and International Patent Application WO95/32738, both incorporated by reference herein.

In one embodiment of the invention the protein comprises the functional domains of a clostridial neurotoxin H chain and some or all of the functions of a clostridial neurotoxin L chain in a single polypeptide chain, and having an inserted proteolytic cleavage site located between the H domain and the L domain by which the single chain protein may be cleaved to produce the individual chains, preferably covalently linked by a disulfide linkage. The invention also includes methods of making such proteins and expressing them within a cell, as well as nucleic acid vectors for the transfer and expression of the nucleotide sequence regions encoding such proteins and cells containing such vectors. The proteolytic cleavage sites comprise amino acid sequences that are selectively recognized and cleaved by a specific enzyme.

In a preferred aspect of the invention, the expressed single-chain proteins comprise the biologically active domains of the H chain and L chain of a clostridial neurotoxin. Scission at the internal proteolytic cleavage site separating the chain domains thus results in the activation of a neurotoxin having full activity.

In another aspect of the invention the single-chain proteins comprise a binding domain targeted to a cell receptor other than one borne by a motor neuron. Such a binding domain may specific bind to, for example, a sensory afferent neuron, or to a non-neuronal cell type or tissue, such as pancreatic acinar cells. The single-chain proteins will contain a translocation domain similar to that of clostridial neurotoxins, and a therapeutic moiety. The therapeutic moiety may be a clostridial neurotoxin light chain, or may be a different therapeutic moiety such as an enzyme, a transcribable nucleotide sequence, growth factor, an antisense nucleotide sequence and the like.

Preferably, the toxins and toxin-based proteins of the present invention will be tailored to contain an additional amino acid sequence comprising a binding tag able to bind a target compound at sufficiently high efficiency to facilitate rapid isolation of the toxin protein. Proteins containing such binding sites are many and well known to those of skill in the art, and may comprise, without limitation, monoclonal antibodies, maltose binding protein, glutathione-S-transferase, protein A, a $His_6$ tag, and the like.

Because such proteins exhibit binding selectivity to a certain compound or compound type, the target compound may be immobilized to a solid support, including without limitation, a chromatography resin or microtiter well and used for affinity purification of the modified toxin. The toxin molecule can then be eluted by standard methods, such as through the use of a high salt solution or specific antagonist.

To minimize the safety risk associated with handling neurotoxin, the toxins of the this aspect of the present invention are expressed as their low activity (or inactive) single-chain proforms, then, by a carefully controlled proteolytic reaction in vitro, they are activated, preferably to the same potency level as the native neurotoxin from which they were derived. To improve the efficiency and rate of proteolytic cleavage the engineered proteolytic cleavage sites can be designed to occur in a specially-designed loop between the H and L portions of the single amino acid chain that promotes accessibility of the protease to the holotoxin substrate.

To reduce the risk of unintentional activation of the toxin by human or commonly encountered proteases, the amino acid sequences of the cleavage site are preferably designed to have a high degree of specificity to proteolytic enzymes which do not normally occur in humans (as either human proteases or occurring in part of the foreseeable human fauna and flora). A non-exclusive list of examples of such proteases includes bovine enterokinase, which cleaves the amino acid sequence DDDDK (SEQ ID NO: 15); tobacco etch virus (TEV) protease, which cleaves the sequences EXXYXQS (SEQ ID NO: 22) and EXXYXQG (SEQ ID NO: 23); GENENASE® from *Bacillus amyliquifaciens*, which cleaves the sequence HY or YH; and PRESCISSION® protease from human rhinovirus 3C, which cleaves the amino acid sequence LEVLFQGP (SEQ ID NO: 16). As used above, the letter X indicates any amino acid. All amino acid sequences shown in the present specification are in the direction from amino terminus to carboxyl terminus, and all nucleotide sequences from 5' to 3', (from left to right) unless otherwise indicated.

In an aspect of the invention the single-chain polypeptide is an isolated polypeptide. By "isolated" is meant removed from its natural environment. For example, for a protein expressed within the cell, isolation includes preparation of a cell lysate as well as subsequent purification steps. A protein expressed extracellularly may be isolated by, for example, separation of the supernatant from the cells as well as any subsequent purification steps.

In another aspect of the invention the interchain loop region of the *C. botulinum* subtype E neurotoxin, which is normally resistant to proteolytic nicking in the bacterium and mammals, is modified to include the inserted proteolytic cleavage site, and this loop region used as the interchain loop region in the single-chain toxin or modified toxin molecules of the present invention. It is believed that using the loop from *C. botulinum* subtype E will stabilize the unnicked toxin molecule in vivo, making it resistant to undesired cleavage until activated through the use of the selected protease.

In yet another aspect of the invention are contemplated compositions comprising recombinant forms of BoNT/E expressed as a single chain polypeptide.

In still another aspect are contemplated recombinant chimeric and/or modified toxin derivatives expressed as a single chain polypeptide. Such polypeptide may be molecular tranporters, such as, without limitation, those disclosed in Dolly et al., European Patent Specification EP 0 760 681 B1, incorporated by reference herein.

In a further aspect the invention includes neurotoxin derivatives comprising at least a portion of a light chain from one clostridial neurotoxin or subtype thereof, and at least a portion of a heavy chain from another neurotoxin or neurotoxin subtype, as well as methods for their production. In one embodiment the hybrid neurotoxin may contain the entire light chain of a light chain from one neurotoxin subtype and the heavy chain from another neurotoxin subtype. In another embodiment, a chimeric neurotoxin derivative may contain a portion (e.g., the binding domain) of the heavy chain of one neurotoxin subtype, with another portion of the heavy chain being from another neurotoxin subtype. Similarly or alternatively, the therapeutic element may comprise light chain portions from different neurotoxins.

Such hybrid or chimeric neurotoxin derivatives are useful, for example, as a means of delivering the therapeutic benefits of such neurotoxins to patients who are immunologically resistant to a given neurotoxin subtype, to patients who may have a lower than average concentration of receptors to a given neurotoxin heavy chain binding moiety, or to patients who may have a protease-resistant variant of the membrane or vesicle toxin substrate (e.g., SNAP-25, VAMP and syntaxin). Creation of recombinant chimeric or hybrid neurotoxin derivatives having a light chain with different substrate would permit such patients to respond to neurotoxin therapy.

With regard to immunological resistance, it is known that most neurotoxin epitopes exist on the heavy chain portion of the toxin. Thus if a patient has neutralizing antibodies to, for example BoNT/A, a chimeric neurotoxin containing the heavy chain from BoNT/E and the light chain from BoNT/A (which has a longer duration of therapeutic activity than other neurotoxin light chains) would overcome this resistance. Likewise if the patient has few cell surface receptors for BoNT/A, the chance are great that the same patient would have adequate receptors to another BoNT subtype. By creating a hybrid or chimeric neurotoxin (such as one containing at least a portion of a heavy chain selected from the group consisting of $HC_A$, $HC_B$, $HC_{C1}$, $HC_D$, $HC_E$, $HC_F$, and $HC_G$ and a at least a portion of a light chain selected from a different clostridial neurotoxin subtype, said light chain being selected from the group consisting of $LC_A$, $LC_B$, $LC_{C1}$, $LC_D$, $LC_E$, $LC_F$, and $LC_G$) combining the heavy chain of that subtype with the most therapeutically appropriate light chain (for example, the BoNT/A light chain) the patient could better respond to neurotoxin therapy.

Another advantage of the hybrid or chimeric neurotoxin derivatives described above is related to the fact that certain of the light chains (e.g., $LC_A$) have a long duration of action, others having a short duration of action (e.g., $LC_E$ AND $LC_F$) while still others have an intermediate duration of activity (e.g., $LC_B$). Thus, hybrid and chimeric neurotoxins represent second and third generation neurotoxin drugs in which the neurotoxin activity may be tailored to a specific therapeutic need or condition, with different drugs having different activities, substrate specificities or duration of activity.

Such hybrid or chimeric neurotoxins would also be useful in treating a patient (such as a soldier or laboratory worker) who has been inoculated with the pentavalent BoNT vaccine.

Such vaccines do not contain BoNT/F; thus, combining the appropriate light chain with the BoNT/F heavy chain would create a therapeutic agent which is effective in such a patient where current therapeutic neurotoxins may not be.

The same strategy may be useful in using derivatives of clostridial neurotoxins with a therapeutic moiety other than an active neurotoxin light chain. As the heavy chain of such an agent would be derived from a neurotoxin, it may be advantageous to use a lesser known, or rarer heavy chain to avoid resistance mechanisms neutralizing the effectiveness of the therapeutic neurotoxin derivative.

By the same token, the binding moiety may be one other than a binding moiety derived from a clostridial neurotoxin heavy chain, thus providing a targeting function to cell types other than motor neurons.

Also included herein are methods for the construction, expression, and purification of such molecules in high yield as biologically active entities.

BRIEF DESCRIPTION OF THE DRAWINGS

FIG. 2A is a representation of a Western blot of an SDS-PAGE gel of cell extracts of *E. coli* JM 109 transformants containing 2 different recombinant single-chain toxins, either before or after induction of plasmid protein expression with IPTG. The antibody used for detection is an anti-His$_6$ monoclonal antibody.

FIG. 2B is a Western blot of IPTG-induced cell extracts from cells transformed with the E234A construct.

FIG. 3A shows the results of an experiment in which affinity purified recombinant single-chain (SC) TeTx is nicked with enterokinase, then separated using SDS-PAGE and visualized using Commassie Brilliant Blue under reducing and non-reducing conditions.

FIG. 3B shows the results of an experiment in which affinity purified recombinant single-chain (SC) TeTx is nicked with enterokinase, then separated using SDS-PAGE under reducing and non-reducing conditions and subjected to a Western blot using anti TeTx heavy chain antibody.

FIG. 4 is a plot of the degree of paralysis induced in a nerve/muscle preparation in vitro using native TeTx, and recombinant single chain neurotoxin before, and after nicking as a function of time.

FIG. 5 is a depiction of the peptide fragments generated upon incubation of the recombinant single-chain TeTx with trypsin and Arg C protease, and deduction, from the N-terminal sequences of one of the resulting fragments, of the amino acid sequence recognized by these agents.

FIG. 7 shows the inhibitory effect upon TeTx stimulated inhibition of Ca$^{++}$-dependent neurotransmitter release of pre-incubating cerebellar cells with the E234A mutant TeTx. Pre-incubation of cerebellar neurons with nicked (FIG. 7A) or unnicked (FIG. 7B) TeTx E234A at 4° C. followed by the addition of 0.2 nM native toxin, antagonized the native toxin's inhibition of transmitter release at 37° C. to similar extents.

FIG. 10 shows the scheme for construction of a plasmid encoding single-chain BoNT/E, and an agarose gel electrophoretogram of the PCR fragment obtained during the construction of the plasmid.

FIG. 12 shows the expression and purification scheme for recombinant single-chain BoNT/E, and a SDS-PAGE electrophoretogram and Western blot of the purification fractions.

FIG. 13 shows SDS-PAGE electrophoretograms under reducing and non-reducing conditions of native recombinant unnicked, and recombinant nicked BoNT/E, and Western Blots directed towards the heavy and light chains of the toxin.

FIG. 15 shows the effect upon Ca++-dependent glutamate release of incubating cerebellar cells with native BoNT/E, un-nicked recombinant single chain BoNT/E, and nicked recombinant single chain BoNT/E.

DETAILED DESCRIPTION OF THE INVENTION

Figure 1A:
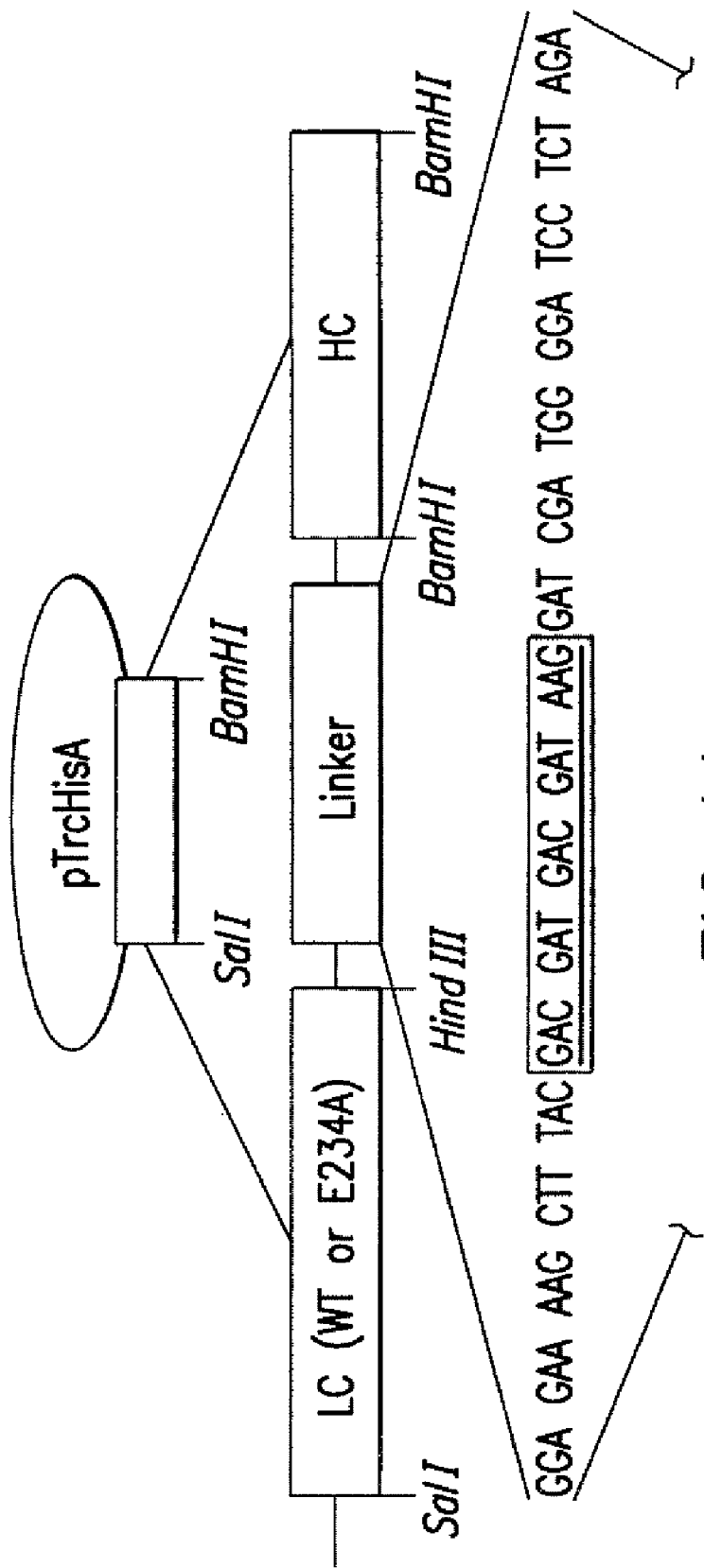
FIG. 1A is a diagrammatic view of the single-chain TeTx construct in plasmid pTrcHisA and the nucleotide sequence of the junction region.

The compositions and methods of the present invention involve modified neurotoxins, their synthesis and use. Di-chain neurotoxins that are normally activated by scission of a single chain polypeptide by indigenous proteases can be modified at the nucleic acid level by alteration or removal of the nucleotide sequence encoding the indigenous protease cleavage site and insertion of a nucleotide sequence encoding another different proteolytic cleavage site resistant to cleavage by host cell or human proteases. The inserted amino acid sequence is designed to be cleaved in vitro through the use of a cleaving agent chosen in advance of expression that is absent from both human and host cell tissue.

The inserted amino acid sequence may be chosen to confer susceptibility to a chemical agent capable of cleaving peptide bonds, such as cyanogen bromide. However, and much more preferably, the encoded amino acid sequence may comprise a proteolytic cleavage site highly specific for a selected protease. The selected protease is one not normally present in the cell expressing the single chain toxin molecule (for example, *E. coli* or the native clostridial bacterium).

In another aspect, the invention is drawn to recombinant single-chain modified clostridial neurotoxins that may be cleaved at will by a protease to provide an active di-chain molecule. Such modified neurotoxins need not be toxic; in certain of these proteins the enzymatic activity of the toxin L chain may be abrogated, and the toxin joined to a drug or other bioactive agent having therapeutic activity. Alternatively, in certain other modified neurotoxins the L chain is enzymatically active, but portions of the H chain are modified to provide specificity to target cells other than the natural target of the neurotoxin, while maintaining the translocation and endocytosis-stimulating activities of the native toxin.

Modified neurotoxins such as those described in this aspect of the invention are disclosed in, for example, International Patent Publications WO95/32738, WO 99/55359, WO96/33273, WO98/07864 and WO99/17806, these publications are incorporated by reference herein. The present invention provides single-chain, cleavable versions of these molecules and improved methods of making such molecules.

In another aspect, the invention comprises a modified clostridial neurotoxin derived from tetanus toxin (TeTx), or one or more of the botulinum toxin (BoNT) subtypes in which the naturally-occurring interchain loop region has been replace with a modified loop region comprising a different amino acid sequence conferring 1) resistance to cleavage by host proteases or autolytic action, and/or 2) lability to a selected protease. Preferably the cleavage site is highly specific for the selected protease.

The interchain loop region of certain clostridial neurotoxins, for example, BoNT/E, is naturally resistant to proteolytic cleavage in vivo. This protease resistance may reflect a secondary or tertiary structure that makes the loop more resistant to indigenous proteases than other clostridial neurotoxins. In one embodiment of the present invention, therefore, the interchain loop region of BoNT/E is substituted for the natural loop region occurring in another BoNT having greater therapeutic activity or duration of action, for example BoNT/A or /B. In another embodiment of the invention the loop region of BoNT/E is modified to contain a proteolytic cleavage site highly specific to a selected protease prior to the subcloning. The otherwise highly conserved BoNT/E loop region would be resistant to indigenous proteases, or those encountered within a human, but would retain the ability to be activated by digestion with the selected protease.

Essentially, the selected protease therefore acts as an "activator" of neurotoxin toxicity (or modified toxin activity) that can be added at will following recombinant expression.

The selected protease may be any protease that recognizes a specific amino acid sequence and cleaves a peptide bond near or at that location, but the selected protease is very preferably not a human protease such as human trypsin, chymotrypsin or pepsin, or a host cell protease. Moreover, the selected protease does not recognize the same amino acid sequence as the indigenous proteases. Finally, the selected protease should not be one expressed by the host cell that contains the plasmid encoding the recombinant neurotoxin.

Any non-human protease recognizing a relatively rare amino acid sequence may be used, provided that the amino acid recognition sequence is also known. Examples of proteases to be selected as activators may include any of the following, without limitation: bovine enterokinase, plant proteases such as papain (from *Carica papaya*) and legumain, insect papain homolog (from the silkworm *Sitophilus zeamatus*), and crustacean papain homolog (decapod), Tobacco etch virus (TEV) protease, which cleaves the sequences EXXYXQS (SEQ ID NO: 22) and EXXYXQG (SEQ ID NO: 23); GENENASE® from *Bacillus amyliquifaciens*, which cleaves the sequence HY or YH; and PRESCISSION® protease from human rhinovirus 3C, which cleaves the amino acid sequence LEVLFQGP (SEQ ID NO: 16). As used above, the letter X indicates any amino acid.

Unless indicated otherwise, the following terms have the following meanings in this specification:

By "binding element" is meant an amino acid sequence region able to preferentially bind to a cell surface marker characteristic of the target cell under physiological conditions. The cell surface marker may comprise a polypeptide, a polysaccharide, a lipid, a glycoprotein, a lipoprotein, or may have structural characteristics of more than one of these. By "preferentially interact" is meant that the disassociation constant ($K_d$) of the binding element for the cell surface marker is at least one order of magnitude less than that of the binding element for any other cell surface marker. Preferably, the disassociation constant is at least 2 orders of magnitude less, even more preferably the disassociation constant is at least 3 orders of magnitude less than that of the binding element for any other cell surface marker to which the neurotoxin or modified neurotoxin is exposed.

The "translocation element" comprises a portion of a clostridial neurotoxin H chain having a translocation activity. By "translocation" is meant the ability to facilitate the transport of a polypeptide through a vesicular membrane, thereby exposing some or all of the polypeptide to the cytoplasm. In the various botulinum neurotoxins translocation is thought to involve an allosteric conformational change of the heavy chain caused by a decrease in pH within the endosome. This conformational change appears to involve and be mediated by the N terminal half of the heavy chain and to result in the formation of pores in the vesicular membrane; this change permits the movement of the proteolytic light chain from within the endosomal vesicle into the cytoplasm. See e.g., Lacy, et al., *Nature Struct. Biol.* 5:898-902 (October 1998).

The amino acid sequence of the translocation-mediating portion of the botulinum neurotoxin heavy chain is known to those of skill in the art; additionally, those amino acid residues within this portion that are known to be essential for conferring the translocation activity are also known.

It would therefore be well within the ability of one of ordinary skill in the art, for example, to employ the naturally occurring N-terminal peptide half of the heavy chain of any of the various *Clostridium tetanus* or *Clostridium botulinum* neurotoxin subtypes as a translocation element, or to design an analogous translocation element by aligning the primary sequences of the N-terminal halves of the various heavy chains and selecting a consensus primary translocation sequence based on conserved amino acid, polarity, steric and hydrophobicity characteristics between the sequences.

The "therapeutic element" of the present invention may comprise, without limitation: active or inactive (i.e., modified) hormone receptors (such as androgen, estrogen, retinoid, perioxysome proliferator and ecdysone receptors etc.), and hormone-agonists and antagonists, nucleic acids capable being of being used as replication, transcription, or translational templates (e.g., for expression of a protein drug having the desired biological activity or for synthesis of a nucleic acid drug as an antisense agent), enzymes, toxins (including apoptosis-inducing or -preventing agents), and the like.

In a preferred embodiment, the therapeutic element is a polypeptide comprising a clostridial neurotoxin light chain or a portion thereof retaining the SNARE-protein sequence-specific endopeptidase activity of a clostridial neurotoxin light chain. The amino acid sequences of the light chain of botulinum neurotoxin (BoNT) subtypes A-G have been determined, as has the amino acid sequence of the light chain of the tetanus neurotoxin (TeTx). Each chain contains the $Zn^{++}$-binding motif His-Glu-X-X-His SEQ ID NO: 17 (N terminal direction at the left) characteristic of Zn++-dependent endopeptidases (HELIH SEQ ID NO: 25 in TeTx, BoNT/A /B and /E; HELNH SEQ ID NO: 26 in BoNT/C; and HELTH SEQ ID NO: 27 in BoNT/D).

Recent studies of the BoNT/A light chain have revealed certain features important for the activity and specificity of the toxin towards its target substrate, SNAP-25. Thus, studies by Zhou et al. *Biochemistry* 34:15175-15181 (1995) have indicated that when the light chain amino acid residue $His_{227}$ is substituted with tyrosine, the resulting polypeptide is unable to cleave SNAP-25; Kurazono et al., *J. Biol. Chem.* 14721-14729 (1992) performed studies in the presynaptic cholinergic neurons of the buccal ganglia of *Aplysia californica* using recombinant BoNT/A light chain that indicated that the removal of 8 N-terminal or 32 C-terminal residues did not abolish toxicity, but that removal of 10 N-terminal or 57 C-terminal residues abolished toxicity in this system. Most recently, the crystal structure of the entire BoNT/A holotoxin has been solved; the active site is indicated as involving the participation of $His_{222}$, $Glu_{223}$, $His_{226}$, $Glu_{261}$ and $Tyr_{365}$. Lacy et al., supra. (These residues correspond to $His_{223}$, $Glu_{224}$, $His_{227}$, $Glu_{262}$ and $Tyr_{366}$ of the BoNT/A L chain of Kurazono et al., supra.) Interestingly, an alignment of BoNT/A through E and TeTx light chains reveals that every such chain invariably has these residues in positions analogous to BoNT/A. Kurazono et al., supra.

The catalytic domain of BoNT/A is very specific for the C-terminus of SNAP-25 and appears to require a minimum of 17 SNAP-25 amino acids for cleavage to occur. The catalytic site resembles a pocket; when the light chained is linked to the heavy chain via the disulfide bond between $Cys_{429}$ and $Cys_{453}$, the translocation domain of the heavy chain appears to block access to the catalytic pocket until the light chain gains entry to the cytosol. When the disulfide bond is then reduced, the catalytic pocket is "opened" and the light chain is fully active.

As described above, VAMP and syntaxin are cleaved by BoNT/B, D, F, G and TeNT, and $BoNT/C_1$, respectively, while SNAP-25 is cleaved by BoNT/A E and C1. The substrate specificities of the various clostridial neurotoxin light chains other than BoNT/A are known. Therefore, the person of ordinary skill in the art could easily determine the toxin residues essential in these subtypes for cleavage and substrate recognition (for example, by site-directed mutagenesis or deletion of various regions of the toxin molecule followed by testing of proteolytic activity and substrate specificity), and could therefore easily design variants of the native neurotoxin light chain that retain or lack the same or similar activity.

In a particularly preferred embodiment, the single chain neurotoxin or neurotoxin derivative of the invention, altered as indicated above, is further modified to remove other incidental endogenous proteolytic sites such as those cleaved by trypsin, Arg C protease, chymotrypsin, or host cell proteases. As indicated below, modification of the primary amino acid sequences in these regions to confer protease resistance can increase the yield of the neurotoxin and reduce the toxicity of the single chain neurotoxin prior to cleavage and activation.

The amino acid sequences recognized by many proteases, and their cleavage specificity are well-known to those of skill in the art. Thus, both the design of a specific proteolytic cleavage site in the loop region between the L and H chain portions of the single-chain toxin and the modification of incidental protease sites in the polypeptide to be protease-resistant is a routine matter of comparing the specificity and recognition sequences for various proteins. In the first case, the specificity of a candidate proteolytic site need not be totally exclusive, but merely needs to exclude cleavage sites for human and/or host cell proteases that might be present during the handling, storage and purification of the single chain neurotoxin. Of course, it is preferable that the protease site is as specific as possible. In the latter case, the modification of the proteolytic cleavage site need only be sufficient to render the site resistant to the activator protease and to human and host cell proteases.

In another preferred embodiment, the recombinant modified single chain neurotoxin is further modified by joining the chain to a binding tag comprising one member of a specific binding complex. By "specific binding complex" is meant two or more chemical or biochemical entities that will bind each other under defined environmental conditions and which will not significantly bind other chemical or biochemical entities present in the environment under the same conditions. Examples of members of a specific binding complex include, without limitation, an antibody and its antigen, a lectin and its target carbohydrate, a nucleic acid strand and its complementary nucleic acid strand, a cell surface receptor and its ligand, a metal and a compound able to form a coordination or chelation complex with that metal, and the like.

In this embodiment, the binding tag may be joined to the single chain toxin through a linker, preferably a cleavable linker. Examples of possible linkers, while not an exhaustive list, include 1) aliphatic dicarboxylic acids of the formula $HOOC-(CH_2)_n-COOH$, where n=1-12 (may be linked at a free amino group); 2) $HO-(CH_2)_n-COOH$, where n>10 (suitable for attachment at the amino terminus of the polypeptide), 3) substituted polybenzene structures, and 4) a N-hydroxysuccinimide (NHS) ester linker. The use of an linker containing an ester permits cleavage of the ester linker following use in the purification of the single chain neurotoxin under relatively mild acidic conditions.

Alternatively, and most preferably, the binding tag may comprise some or all of the amino acid sequence of an appropriately chosen polypeptide coexpressed with the single chain toxin as a fusion protein; such polypeptides may comprise, without limitation, the maltose binding domain of maltose binding protein (MBP); a $His_6$ tag (a run of 6 histidine residues); the calmodulin binding domain of calmodulin binding protein; and the glutathione binding domain of glutathione-S-transferase. Other polypeptide binding tags are well known to those of skill in the art, and can easily be adapted for use in the present invention.

Additionally, the binding tag may be constructed to have a protease cleavage site between itself and either the amino terminus or the carboxyl terminus of the single chain toxin so as be removable following purification of the peptide. The proteolytic cleavage site may be designed to be cleaved by the same activator protease chosen to nick the single chain toxin between the H and L chains.

It is therefore an object of the invention to provide a recombinant activatible single chain neurotoxin molecule that has reduced toxicity compared to the native neurotoxin until activated by reaction with a non-clostridial protease. The single chain neurotoxin is more easily purified, is less dangerous to handle in the purification process, and can be optionally modified to give the toxin more desirable properties.

It is also an object of the invention to provide a method of making a recombinant activatable single chain neurotoxin by modifying the nucleotide sequence encoding the neurotoxin to replace the native amino acid proteolytic cleavage sequence separating the H and L chain with an amino acid sequence stable to indigenous clostridial or host cell proteases but susceptible to cleavage by chosen protease in vitro.

It is further an object of the present invention to provide more stable neurotoxin polypeptides through modification of the nucleotide sequence of the coding region of the H and L chains thereof, removing incidental proteolytic cleavage sites by causing the replacement of labile amino acids with other amino acid residues which confer upon the toxin resistance to undesired proteolytic degradation.

Additionally, it is an object of the invention to provide methods of purifying recombinant neurotoxins as a single chain by joining the expressed single chain neurotoxin to a binding moiety comprising partner of a specific binding complex which can be used in the affinity purification with the binding partner comprising the other half of the binding complex. Purification can be performed batch-wise or in a chromatography column. The binding moiety may then be removed following the affinity step, and separated from the neurotoxin.

It is also an object of the invention to provide single-chain recombinant modified neurotoxin molecules for use as therapeutic agents. The modified neurotoxin molecules may have an altered target specificity or an altered activity compared to the native neurotoxin from which it is derived, or both.

It is also an object of the invention to provide a single chain activatable recombinant neurotoxin that may be more easily purified than the wild type neurotoxin. Such a neurotoxin permits the large scale preparation of properly folded highly pure toxin for clinical use.

The following Examples serve to illustrate particular embodiments of the invention, and do not limit the scope of the invention defined in the claims in any way.

Example 1

Construction of an Expression Vector Containing a Single Chain TeTx Coding Region The present invention can be exemplified describing the construction of a plasmid that will express TeTx in *E. coli* as a single protein that is readily purified, i.e., by affinity chromatography. TeTx can be chosen as a pilot system because (i) the availability of an excellent vaccine greatly reduces the risk of its handling and (ii) it is the most comprehensively studied of the toxins in terms of expressing HC and LC domains. However, those of skill in the art will understand that the same or similar strategies may be employed using any dichain or binary toxin or other bioactive molecule expressed as a single polypeptide and activated by proteolytic cleavage. Single chain molecules were constructed containing the wild type TeTx L chain and a mutated version of the TeTx light chain wherein a glutamic acid residue at position 234 is changed to an alanine (termed "E234A", Ala$^{234}$, or "the E234A mutant light chain"), respectively. This latter mutation results in an inactive TeTx light chain, and a plasmid encoding the E234A mutant light chain (pMAL-E234A) was constructed as described in Li et al., Biochemistry 33:7014-7020 (1994) (hereby incorporated by reference herein). The following protocol is used for the construction of each single-chain toxin.

The vector pTrcHisA, purchased from Invitrogen, is modified using a Stratagene QuickChange® site-directed mutagenesis kit (for site-directed mutagenesis techniques, see e.g., Smith et al., *J. Biol. Chem.* 253:6651-6560 (1979); incorporated by reference herein in its entirety) to create two extra restriction sites (SalI and HindIII) upstream of the nucleotides encoding a pre-existing enterokinase (EK) cleavage site. The plasmid also contains a translational start codon (ATG) followed by a run of codons encoding 6 histidine residues immediately upstream of the enterokinase cleavage site. A multiple cloning site containing Bam HI, XhoI, Bgl II, Pst I, Kpn I, Eco RI BstB I and Hind III cleavage sites is located immediately downstream of the EK site; the Hind III site is removed by site-directed mutagenesis. The following primers are employed to insert the restriction sites (underlined) upstream of the EK cleavage site:

```
                                         SEQ ID NO: 1
GACTGGTGGACAGCAAGTCGACCGGAAGCTTTACGACGATGACG,
             Sal I      Hind III
and
                                         SEQ ID NO: 2
CGTCATCGTCGTAAAGCTTCCGGTCGACTTGCTGTCCACCAGTC
             Hind III    Sal I
```

The resulting plasmid contains both Sal I and Hind III sites located at the 5' side of the nucleotide sequence encoding the bovine enterokinase (EK) cleavage site.

The nucleotide sequence encoding the wild-type TeTx L chain is obtained from plasmid pMAL-LC, described in Li et al., *Biochemistry* 33, 7014-7020 (1994), incorporated by reference herein. The plasmid encodes the TeTx light chain as a fusion protein with maltose binding protein (MBP) located immediately upstream of the coding sequence for the L chain. The MBP and L chain portions of the fusion protein are designed to contain the cleavage site for human blood coagulation factor Xa (Ile-Glu-Gly-Arg of SEQ ID NO: 28) to facilitate removal of the MBP once affinity purification has been performed.

The DNA fragment containing the coding sequence of the L chain is excised from plasmid pMAL-LC by digesting the plasmid with Sal I and Hind III, gel purifying the resulting DNA fragment containing the L chain, and ligating this fragment into plasmid pTrcHisA at the newly created Sal I and Hind III sites upstream of the EK site. This fragment results in the excission of the maltose binding protein sequences from the N terminus of the L chain.

An identical procedure is used to subclone the DNA fragment containing a mutant L chain from plasmid pMAL-LC-Ala$^2$, in which a single amino acid change is made at amino acid 234 of the L chain, substituting the native glutamic acid with alanine. This change is sufficient to abrogate the zinc endopeptidase activity of the L chain, and to render non-toxic a reconstituted tetanus toxin containing native H chain and the Ala$^{234}$ L chain.

The DNA fragment containing the H chain is obtained from plasmid pMAL-HC; construction of this vector is described in Li et al., *J. Biochem.* 125:1200-1208 (1999), hereby incorporated by reference herein. Briefly, the gene encoding the H chain is constructed by assembling three DNA fragments containing different portions of the H chain coding sequence which had been cloned into separate plasmids. The fragments comprising the amino terminal half of the H are first amplified using standard polymerase chain reaction methods (see, e.g., Mullis, U.S. Pat. No. 4,683,202 and Mullis et al., U.S. Pat. No. 4,800,159, both incorporated by reference herein in their entirety) and the following primers: PCR primers a (containing a Xba I cleavage site) and b (containing a Bgl II cleavage site) (SEQ ID NO: 3 and 4, respectively) are used to amplify the H chain fragment contained in a plasmid termed pTet8; PCR primers c (containing a Bgl II cleavage site) and d (containing both a Hind III and a Sal I cleavage site) (SEQ ID NO: 5 and 6, respectively) are used to amplify the H chain fragment contained in a plasmid termed pTet14. The nucleotide sequences of these primers are provided below, with restriction sites underlined.

```
                                        SEQ ID NO: 3
AATAGATCTAGATCATTAACAGATTTAGGA              (a)

SEQ ID NO: 4
TTCTAAAGATCTATACATTTGATAACT                 (b)

SEQ ID NO: 5
ATGTATAGATCTTTAGAATATCAAGTA                 (c)

SEQ ID NO: 6
ATCGATAAGCTTTTATCAGTCGACCCAACAATCCAGATTTTTAGA (d)
```

Following PCR amplification and gel purification of the amplified H chain fragments, each fragment is digested with Bgl II and ligated to yield the complete N terminal half of the H chain coding region. This ligation product is then digested with Xba I and Hind III and subcloned into the multiple cloning site of pMAL-c2-T (the plasmid being also cut with Xba I and Hind III), which is located downstream of the coding region for MBP and the factor Xa site. pMAL-c2 is a commecially available vector well known to those of skill in the art. The resulting plasmid is pMAL-$H_N$.

The entire H chain coding region is assembled as follows. The pMAL-$H_N$ plasmid is digested with Sac I and Sal I to yield the DNA fragment encoding the N-terminus of the H chain. Plasmid pTet215 is digested with Sal I and Bam HI to yield the DNA fragment encoding the H chain carboxyl terminus. The vector pMAL-c2-T is digested with Sac I and Bam HI, and ligated to the digested H chain fragments, which will assemble in the proper orientation due to the use of distinct endonucleases. The resulting plasmid is pMAL-HC.

The DNA fragments encoding the H and L chains (including $Ala^{234}$ L chain) are cut and purified directly from pMAL-LC or pMALE234A and pMAL-HC constructs and subcloned into the modified pTrcHisA vector described above. The H chain was first ligated into the modified vector at the Bam HI site immediately downstream of the EK site, and the resulting plasmid was gel purified. Following digestion of this plasmid with Hind III and Sal I, the L chain was ligated at a position just upstream of the EK cleavage site.

The resulting plasmid construct contains the nucleotide sequence encoding the single-chain toxin protein, comprising (from amino to carboxyl terminus): six histidine residues (the His tag), followed by the L chain, an enterokinase cleavage site, and the H chain. The translated junction between the L and H chains containing the EK cleavage site (DDDDK) is shown below (in the direction from N-terminus to C-terminus) and in FIG. 1.

```
                                              SEQ ID NO: 7
                               EK site
   SKLIGLCKKIIPPTNIRENLYNRTA-GEKLYDDDDKDRWGSSR-
          L chain          interchain loop SLTDLGGELCIKNEDLTFIAEKN
       H chain
```

To allow expression of the two chains as a single unit, a nucleotide sequence comprising a stop codon present at the 3' end of the L chain coding sequence in the pMAL-LC is removed by site-directed mutagenesis using two primers (SEQ ID NO: 8 and 9), resulting in a single reading frame containing both H and L chains.

```
                                              SEQ ID NO: 8
AATAGAACTGCAGGAGAAAAGCTTTACGACGATGAC,
and TGATAA
(deleted stop codon; coding strand)

SEQ ID. NO: 9
GTCATCGTCGTAAAGCTTTTCTCCTGCAGTTCTATTTTATCA
(deleted stop codon; non-coding strand)
```

The resulting pTrcHisA-based construct is transformed into *E. coli* strain JM109 by heat shock using the method of Hanahan, and transformant colonies are isolated on Luria agar plates containing 100 μg/ml ampicillin. Plasmids are purified from these transformants and the insertions are confirmed by analytical restriction endonuclease digestion and agarose gel electrophoresis.

Example 2

Expression and Physical Characterization of Single-Chain TeTx

Expression of the pTrcHisA-based single chain TeTx construct (under control of a hybrid trp/lac promoter) is induced by addition of 1 mM IPTG (isopropyl thio-galactopyranoside) to a confluent culture of a representative transformant clone in 200 ml Luria broth containing 100 μg/ml ampicillin and incubating further at 37° C. for 16 hours before cell harvest by centrifugation.

The cell pellets are resuspended in 30 ml Buffer A (20 mM $Na_2PO_4$, 500 mM NaCl (pH 7.8)), then lysed by ultrasonication at 4° C., using 10-second bursts at a medium setting. Insoluble debris is removed by centrifugation at 9,000×g for 30 min at 4° C., and the supernatant recovered by centrifugation.

The supernatant containing each single chain construct is incubated for 20 minutes at 22° C. with 2 ml of nickel-ion resin (Invitrogen Corp.) for affinity purification by means of chelation between the histidine residues at the amino terminus of the single chain toxin molecule and the nickel. The resins were then load onto mini columns and washed with 200 ml of washing buffer (20 mM $Na_2PO_4$, 500 mM NaCl (pH 6.0)) to remove any non-specifically bound material, the recombinant single-chain proteins are eluted on 0.5 ml fractions with 8-15 ml of 100 mM imidazole in Buffer A. The concentration of the eluted single-chains was measured by Bradford's protein assay (Bio-Rad Laboratories); approximately 1 milligram of the fusion protein was recovered.

Example 3

SDS-PAGE and Western Blot Analysis of Recombinant Single-Chain TeTx

The single-chain TeTx constructs are grown in Luria broth containing ampicillin at 37° C., and aliquots taken both before and after induction of protein expression with IPTG. Crude cell extracts are prepared for SDS-PAGE by dilution in sample buffer under reducing conditions in the presence of β-mercaptoethanol (BME). Following SDS-PAGE electrophoresis, the separated proteins are Western-blotted as follows: the proteins are electrophoretically transferred to a polyvinylidenedifluoride (PVDF) membrane using standard methods (see, e.g., Sambrook et al., *Molecular Cloning, A Laboratory Manual* (2d ed. Cold Spring Harbor Laboratory Press 1989), hereby incorporated by reference in its entirety), the membrane treated to reduce background Ig binding, and then probed using an anti-His$_6$ antibody, followed by detection using an alkaline phosphatase-conjugated secondary antibody and development with a 5-bromo-4-chloro-3-indolyl-phosphate/nitro blue tetrazolium substrate.

As shown in lanes 1 and 2 of FIG. 2A, the Western blot revealed no detectable TeTx expression before induction of protein synthesis; by contrast, a single band of approximate molecular weight 150 kDa was revealed in the aliquots taken following protein induction (See lanes 3 and 4.) In FIG. 2A, lanes 1 and 3 are the WT light chain construct and lanes 2 and 4 contain the E234A mutant construct.

FIG. 2B is a Western blot of IPTG-induced cell extracts from cells transformed with the E234A construct. Significantly, no discernable lower molecular weight proteolytic cleavage products of the light chain were observed, providing evidence for the relative stability of the single-chain toxin following expression and purification.

FIG. 3 shows the results of a second experiment, in which affinity purified recombinant single-chain (SC) TeTx is nicked with enterokinase as follows. Thirty micrograms of purified single chain toxin are incubated with 1 unit of enterokinase in a solution containing 50 mM Tris-HCl (pH 8.0), 1 mM CaCl$_2$ and 0.1% TWEEN-20® (v/v) (polyoxyethylene (20) sorbitan monolaureate). As a control, the recombinant protein is incubated in the same reaction mixture containing no EK. These samples, plus an aliquot of native (non-recombinant) TeTx are subjected to SDS-PAGE in an 8% polyacrylamide gel under either reducing (+BME) or non-reducing (−BME) conditions. The resulting gel is used both for a Western blot and subsequent detection using anti-H claim antibodies (FIG. 3B), and direct staining with Coomassie Blue (FIG. 3A).

As indicated by FIG. 3, under non-reducing conditions all three samples (Native TeTx (Lane 1), unnicked recombinant toxin (Lane 2), and enterokinase nicked recombinant toxin (Lane 3)) will migrate as doublets (apparently different conformers that resolve into a single band upon reduction) with essentially indistinguishable apparent molecular weights of about 150 kDa. The non-reducing gel confirms that 1) high levels of expression are obtained, 2) the disulfide bonds linking the light and heavy chains are fully formed, and 3) the recombinant single chain toxin is not subject to observable proteolytic degradation.

By contrast, under reducing conditions wild-type and nicked recombinant toxin yield an H chain having a molecular weight of about 100 kDa by both Western blot and Coomassie staining. Additionally, in the Coomassie stained gel, both of these samples also show a lower molecular weight species of about 50 kDa, corresponding to the L chain. The wild-type L chain will migrate with a lower apparent molecular weight than that of the recombinant L chain, which has 22 additional amino acid residues due to the presence of the His$_6$ moiety and a modified EK cleavage site-containing interchain junction region. The unnicked recombinant toxin (Lane 2) migrates as a single band with an apparent molecular weight of about 150 kDa. Notably, no trace of the unnicked toxin is seen in lane 3, indicating the effectiveness of enterokinase treatment.

Example 4

In Vitro Toxin-Induced Paralysis by Recombinant Single-Chain TeTx a) The biological activity of the recombinant TeTx is also examined and compared to wild-type toxin using mouse phrenic nerve hemi-diaphragm, since the native toxin is known to cause neuromuscular paralysis, albeit at higher concentrations than act in the CNS. For this experiment, mouse left phrenic nerve-hemidiaphragm is dissected from mice (T/O strain, 4-week old and ~20 g in weight) and immediately transferred into a closed circulatory superfusion system containing 10 ml of Krebs-Ringer solution (118 mM NaCl, 4.7 mM KCl, 1.2 mM MgSO$_4$, 2.5 mM CaCl$_2$, 23.8 mM NaHCO$_4$, 1.2 mM KH$_2$PO$_4$, 11.7 mM glucose (pH 7.4)), bubbled with 95% O$_2$ and 5% CO$_2$ and supplemented with 0.1% (w/v) bovine serum albumin to diminish non-specific adsorption of the toxins (Li et al., Biochemistry 33:7014-7020 (1994)). The hemidiaphragms are kept in a bath containing 10 ml Krebs-Ringer buffer at 37° C. for 10 minutes before being exposed to 4 or 10 nM native TeTx (▼ and ∇, respectively) or 10 nM nicked recombinant TeTx (●) or 10 nM un-nicked recombinant TeTx (○), respectively. (See FIG. 4).

Muscle twitch is evoked by supra-maximal stimulation of the phrenic nerve with bipolar electrodes and recorded via a force-displacement transducer (Lectromed, UK) connected to an amplifier and computer system (MacLab, AD Instruments, UK). Parameters of nerve stimulation are 0.2 Hz square waves of 0.1 msec duration with 1.5-2.5 V amplitude. Toxin-induced paralysis of neuromuscular transmission is quantified as the time required for nerve-evoked muscle contraction to decrease to 10% (90% reduction) of the original value.

As shown in FIG. 4, 10 nM recombinant nicked TeTx was found to be as potent as 10 nM native toxin in blocking nerve-induced muscle twitch, with the preparations yielding a 90% reduction in muscle tension in approximately 170 minutes. Thus, this novel preparation of TeTx expressed in *E. coli* at high level as a single-chain, activatable polypeptide and purified by a simple affinity chromatography step proved to be fully active by all the criteria examined.

By contrast, 10 nM of the unnicked TeTx preparation require approximately twice as long to reduce muscle tension, and was approximately as active as 4 nM of the wild-type TeTx. As a control, hemidiaphragms incubated with KR buffer and the trace amount of enterokinase present in the experimental samples were found to show negligible decrease in muscle tension over 5 hrs.

Thus, this experiment indicates that the unnicked TeTx is considerably less toxic that either the wild type or recombinant nicked protein in vitro.

Example 5

Further Modification of Single Chain TeTx to Remove Proteolytic Cleavage Sites Reduces Toxicity of Unnicked Recombinant Toxin While the unnicked recombinant single-chain form of TeTx displays reduced toxicity as compared to the nicked form, the residual toxin activity probably arises from activation of the toxin by additional proteases in vivo. To test this possibility, sites in the single chain toxin molecule susceptible to proteolytic cleavage by trypsin and Arg C protease are identified by incubation of single-chain TeTx with these enzymes as follows. Fifty micrograms μg of recombinant single chain TeTx is incubated with 4 μg of Arg-C at 37° C. for 4 h; 0.1 μg of trypsin at 37° C. for 0.5 h; or buffer without protease as a control. These reactions are terminated by the addition of SDS-PAGE sample buffer containing 0.1% SDS followed by boiling for 5 minutes; then the samples are subjected to SDS-PAGE, followed by a Western electrophoretic transfer to a polyvinylidenedifluoride (PVDF) membrane. The membrane is blotted with IgG specific for the His$_6$-tag and detected using a horseradish peroxidase staining system.

As shown in FIG. 5, the Western blot reveals that trypsin and Arg C protease yielded a L chain (and thus a H chain) fragment of the same size. Additionally, the transfer of a duplicate gel was stained for protein with Ponceau red and the H chain band of approximate molecular weight 100 kDa was excised from each lane and analysed by N-terminal sequencing.

Figure 1B:
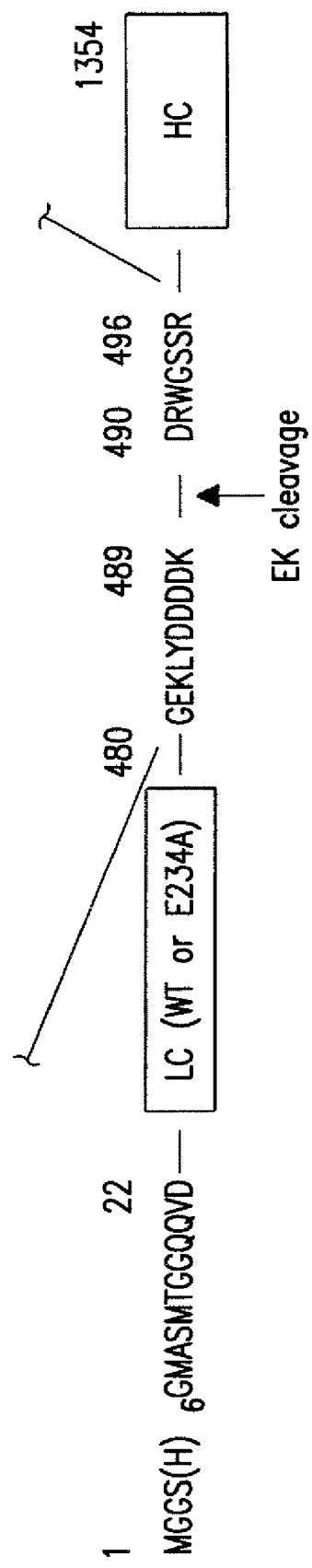
FIG. 1B shows the and amino acid sequence connecting the carboxyl terminus of the L chain and the amino terminus of the H chain and an engineered loop region containing an enterokinase cleavage site.

In the recombinant single-chain TeTx, the LC and HC are linked by 17 amino acids (GEKLYDDDDKDRWGSSR SEQ ID NO: 29), followed by the beginning of the H chain sequence (SEQ ID NO: 20). N-terminal amino acid sequencing of the larger fragment produced by both trypsin and Arg C protease reveal that first 5 amino acids of the 100 kDa trypsin and Arg C protease cleavage product protein are SLTDL of SEQ ID NO: 30; thus, these proteases appear to cleave the single—chain toxin between the R—S bond (see FIG. 1) so as to liberate the H chain and the L chain containing the EK linker at its C terminus, with this variant therefore yielding a dichain toxin essentially identical to the EK nicked toxin.

The arginine at the carboxy terminus of the EK linker sequence is mutated by site-directed mutagenesis to a glycine (R496G), and the resulting single chain toxin polypeptide is expressed and purified as above.

Figure 6:
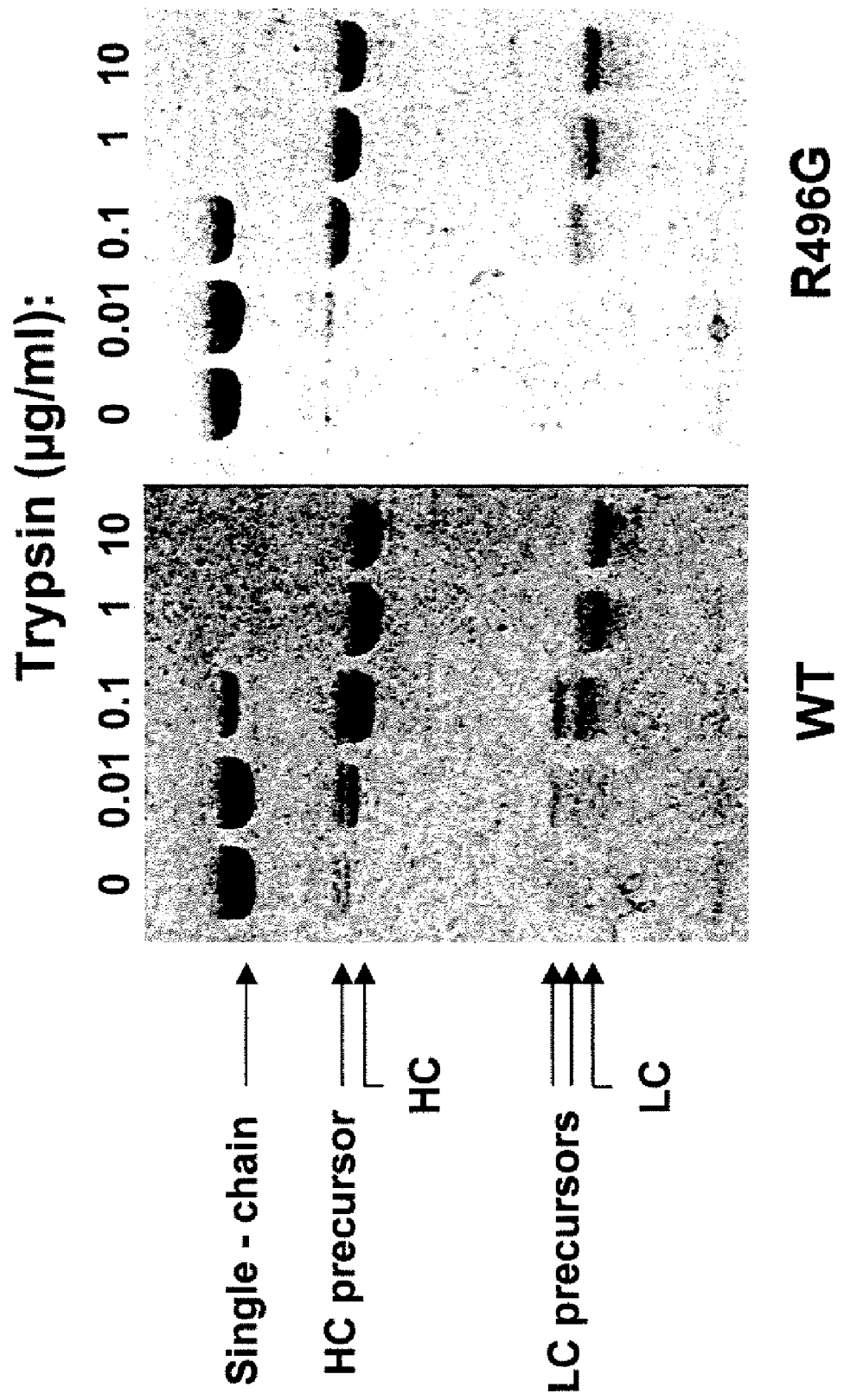
FIG. 6 shows the digestion of unnicked SC WT TeTx and SC R496G TeTx with various concentrations of trypsin.

Titration of the 6 micrograms of the R496G mutated single chain (WT LC) toxin and the SC TeTx lacking such a mutation against 0, 0.01, 0.1, 1, 10 µg/ml of trypsin, followed by SDS-PAGE and staining with Coomassie Brilliant Blue, yields the cleavage pattern seen in FIG. 6. As can be seen, both single chain molecules are susceptible to typsin cleavage; however the R496G mutant yields fewer fragments than the SC toxin not containing a mutation in the loop region between the chains. For example, while three trypsin peptide bands can clearly be seen near the light chain band upon trypsin cleavage of the SC WT toxin, only two such bands are seen in the R496G digests.

The fact that there exist remaining trypsin sites in the R496G mutant SC toxin probably accounts for the fact that this mutant does not cause the lowering of toxicity as compared to the un-nicked SC toxin; both preparations give similar values in the mouse lethality and neuromuscular paralysis assays described above.

A different assay system is used to measure neurotoxin activity toward CNS neurons, the cells naturally affected by TeTx. The cells used are cerebellar neurons; these cells are disassociated from the cerebella of 7 day old rats. Neurons are suspended at 1–2×10$^6$/mL in medium consisting of 3 parts Basal Eagle Medium and 1 part of a buffer consisting of 40 mM HEPES-NaOH (pH 7.3), 78.4 mM KCl, 37.6 mM D-glucose, 2.8 mM CaCl$_2$, 1.6 mM MgSO$_4$ and 1.0 mM NaH$_2$PO$_4$, as well as 1×N2 supplement, 1.0 mM L-glutamine, 60 units/mL penicillin, 60 µg/mL streptomycin and 5% (v/v) dialysed horse serum. One milliliter of this cell suspension is added to 22 mm diameter poly-D-lysine coated wells. Cytosine β-D-arabinofuranoside (Ara-C, 40 µM) is added after 20-24 hours in 5% (v/v) CO$_2$ culture, and neurons are maintained by weekly replacement of the above-noted medium containing 40 µM Ara-C.

For each assay, neurons are cultured for at least 10 days in vitro are washed four times with O$_2$-gassed Krebs-Ringer HEPES buffer (KRH, mM: 20 HEPES.NaOH pH7.4, 128 NaCl, 5 KCl, 1 NaH$_2$PO$_4$, 1.4 CaCl$_2$, 1.2 mM MgSO$_4$, 10 D-glucose and 0.05 mg/mL BSA), and 0.5 mL of the latter buffer containing 0.25 µCi/mL [14C]-glutamine (i.e. the glutamate precursor) is added. All steps are performed at 37° C. After a 45 minute labeling period, the medium is removed and the neurons washed four times as before. Control and toxin-treated neurons are incubated for 5 minutes at 37° C. in KRH buffer containing either 1.4 mM Ca$^{2+}$ or 0.5 mM EGTA (i.e. to assess Ca$^{2+}$-independent release); aliquots are then removed and retained for assessment of [$^{14}$C]-glutamate content by scintillation counting. Immediately after removal of the above basal medium, a modified KRH buffer containing 50 mM KCl (containing a lowered 83 mM NaCl content in order to maintain a normal osmotic potential) and either 1.4 Ca$^{2+}$ or 0.5 mM EGTA are added for a 5 minute stimulation period. Finally, neurons were solubilized with 20 mM EGTA.NaOH pH 7.5 containing 1% (w/v) SDS, and aliquots subjected to scintillation counting in order to calculate their remaining radioactive contents. The amounts of $^{14}$C-glutamate in basal and stimulated samples are expressed as percentages relative to the calculated total cell content. The percentage [$^{14}$C]-glutamate contents in EGTA-containing buffer are subtracted from the values recorded in Ca$^{2+}$-containing samples in order to calculate the relevant Ca$^{2+}$-dependent component of release and in turn the latter basal readings are subtracted from values obtained for 50 mM KCl samples to yield the K$^+$-evoked Ca$^{2+}$-dependent glutamate release component.

Figure 8:
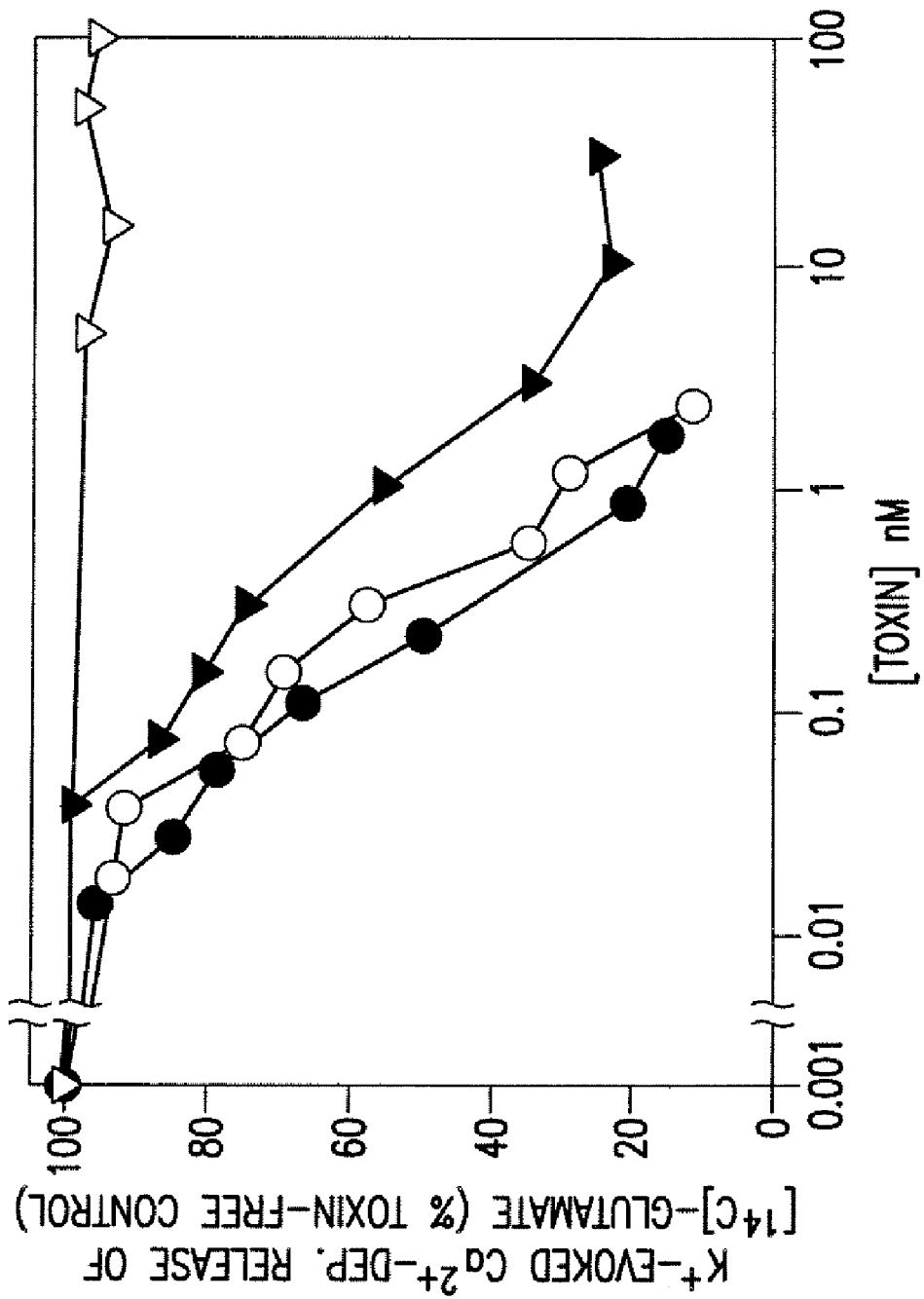
FIG. 8 shows the effect upon Ca$^{++}$-dependent neurotransmitter release of cerebellar neurons upon exposure to native, recombinant E234A mutant single-chain, and the recombinant R496G mutant single chain TeTx.

FIG. 8 demonstrates the ability of the recombinant toxin to inhibit neurotransmitter release. Cerebellar neurons, maintained for 10 days in vitro, were washed twice with ice-cold KRH buffer containing 5 mM Mg$^{2+}$ and 0.5 mM Ca$^{2+}$, then exposed in this buffer to the specified concentrations of (•) native TeTx, (○) EK-nicked TeTx R496G, (▼) single chain unnicked TeTx, or (∇) EK-nicked TeTx E234A for 60 min at 4° C. (see FIG. 8). Native TeTx (0.2 nM) was then added to the wells specified and, after an additional 30 min, the neurons were washed three times with ice-cold KRH buffer and incubated for 30 min at 37° C. Subsequent assessment of K$^+$-evoked Ca$^{2+}$-dependent neurotransmitter release was performed as detailed above. The results of this assay are shown in FIG. 8.

When cerebellar neurons are exposed to nicked recombinant TeTx, a dose-dependent inhibition of Ca$^{++}$ dependent transmitter release is seen with a potency similar to the native toxin. Nicked recombinant SC TeTx, both WT and R496G, gave similar values in this assay. Thus, while toxin activity in the unnicked single chain molecule is not abrogated through the removal of a single trypsin cleavage site, the removal of additional such sites is feasible in regions of the single chain toxin to achieve an activatable single-chain proform of the toxin that exhibits even lower toxicity unless activated in vitro, when its full activity can be achieved.

Example 6

Protease-Deficient TeTx Mutant Antagonises the Actions of TeTx on Peripheral and Central Neurons Table 1 shows the tabulated results of the indicated TeTx constructs tested in three assays of toxin activity: ability to cleave the HV62 peptide (which measures proteolytic activity only); neuromuscular paralysis (which is an indication of the toxin molecules' ability to enter the cell and thence to inhibit neurotransmitter release), and mouse lethality upon intraperitoneal injection of the various toxin constructs. The first two of these assays was performed as described above.

The mouse lethality assay was performed essentially as follows: Samples of recombinant purified single-chain TeTx, R496G mutant TeTx, and E234A mutant TeTx are each divided into two aliquots and one aliquot treated with enterokinase to nick the toxin. All samples are serially diluted into 50 mM phosphate buffer (pH 7.0), 150 mM NaCl and 0.25% (w/v) bovine serum albumin (BSA), and the toxin preparations are injected into mice intraperitoneally.

As shown in Table 1, the native and nicked TeTx preparations were comparably active in the mouse lethality assay, having an $LD_{50}$ of about $1\times10^8$/mg. The unnicked recombinant toxin and unnicked R496G mutant were both about half as active. Finally, the nickedf E234A proteolytically inactive toxin was less than $5\times10^7$ fold less active.

TABLE 1

Biological Activity of SC TeTx wild type and mutants (E234A and R496G) before and after nicking with enterokinase

| Purified TeTx preparations | Initial rate of cleavage[a] of HV62 (nmol. min$^{-1}$mg$^{-1}$) [Relative rate (%)] | Mouse lethality[b] (LD50/ mg) | Time (min.) for 10 nM to cause 90% neuromuscular paralysis |
|---|---|---|---|
| Native | 20.3 ± 0.91 | 1 × 10$^8$ | 145 |
| Un-nicked Sc WT | 8.0 ± 0.03 | 0.5 × 10$^8$ | 260 |
| Nicked[c] SC WT | 22.7 ± 3.37 | 1 × 10$^8$ | 150 |
| Un-nicked SC R496G | 11.7 ± 0.6 | 0.5 × 10$^8$ | 250 ± 15 |
| Nicked[c] SC R496G | 52.3 ± 4.9 | 1 × 10$^8$ | 135 ± 10 |
| Un-nicked SC E234A | ≦0.01[d] | Not tested | Not tested |
| Nicked[c] SC E234A | ≦0.01[1] | <50 | No detectable activity |

[a]Initial rates of proteolysis were measured using the RP-HPLC-based method detailed in Foran et al. (1994). Incubations with 15 μM of a synthetic peptide corresponding to residues 33 to 94 of human VAMP-2 (HV62) were performed at 37° C. in 50 mM HEPES, NaOH pH 7.5 containing 2 mM DTT 0.2 mg · ml$^{-1}$ BSA and 50 μM ZnCl$_2$, using the appropriate concentration of each reduced toxin preparation required to proteolyze 10-15% of the substrate during a 30 min. period. Data are means (±S.D.; n = 4).
[b]LD$_{50}$ is the amount of toxin that killed 50% of the injected mice within 4 days.
[c]Toxin preparations were nicked with EK (1 unit/30 μg) at 22° C. for 1 h.
[d]This v value represents the detection limits of the RP-HPLC assay; no proteolysis of HV62 was observed using prolonged incubations.

Purified SC E234A TeTx, in which the catalytic E at position 234 was replaced by an A, failed to show any detectable proteolysis of a peptide containing residues 33 to 94 of human VAMP-2 (termed HV62), either before or after nicking with EK. Accordingly, nicked TeTx E234A proved to be devoid of toxicity in mice and unable to inhibit transmitter release at the neuromuscular junction or from cerebellar neurons.

Importantly, however, this mutant toxin retained the ability to bind to the cell surface receptors on peripheral and central neurons. Pre-incubation of cerebellar neurons with nicked (10-60 nM) or unnicked (7-40 nM) TeTx E234A at 4° C. followed by the addition of 0.2 nM native toxin, antagonized the native toxin's inhibition of transmitter release at 37° C. to similar extents (FIG. 7).

Figure 9:
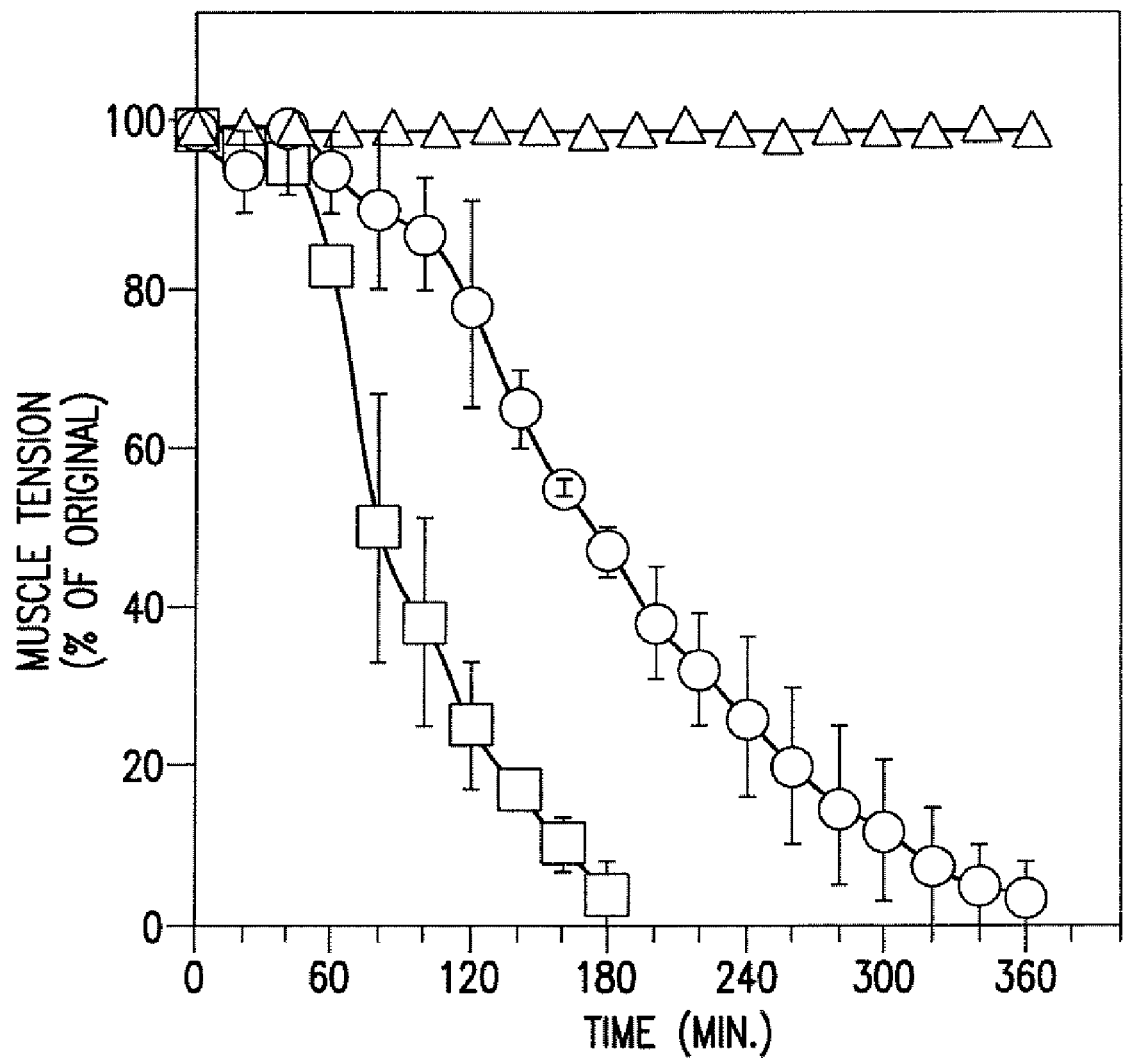
FIG. 9 shows the inhibitory effect upon TeTx-stimulated paralytic activity of preincubating mouse hemi diaphrams with the E234A mutant TeTx.

As demonstrated in FIG. 9, exposure of mouse diaphragm to 100 nM TeTx E234A at 4° C. for 60 minutes prior to adding 1 nM native toxin prolonged the time taken to cause neuromuscular paralysis.

Mouse phrenic-nerve hemi-diaphragm was incubated in KR at 37° C. with 20 nM recombinant TeTx E234A (Δ) whilst stimulating the nerve (0.2 Hz, 1.5-2.5v) and recording muscle tension. For assessing competition, hemi-diaphragms were incubated for 60 minutes at 4° C. with MKR containing 0.1% BSA only (□), or the latter plus 100 nM nicked TeTx E234A (○), before the addition of 1 nM native TeTx. Following 30 minutes exposure to the latter, the tissues were washed three times with MKR and twice with KR. The temperature was raised to 37° C. and the nerve stimulated with recording of the evoked muscle twitch, as outlined above. This apparent competition for toxin binding by the mutant seen with both tissues demonstrates that the recombinant dichain TeTx exhibits much higher affinity for the cell surface receptors than the heavy chain or $H_c$ of TeTx alone. These results suggest that the conformation of the recombinant dichain TeTx has high affinity to the cell surface receptor.

Moreover, and very significantly, these data demonstrate that recombinant molecules can be made according to the inventive methods of the present patent application having specific binding for the same cellular receptor as TeTx. However, such molecules may, like the E234A mutant, be inactive as toxin molecules but will retain the ability to be taken up by the target cell; thus serving as potential transporter molecules.

Example 7

Expression of Single Chain BoNT/A

Using methods similar to those described above, DNA fragments containing the BoNT subtype A neurotoxin H and L chains were ligated together, separated by the EK cleavage site. This single-chain toxin coding sequence was inserted into a variety of expression vectors containing different N terminal sequences and promoters, as shown in Table 2, below.

TABLE 2

| Vector | Promoter | Fusion Tag | Tag Size (amino acids) | Fusion Size (kDa) | E. coli strain |
|---|---|---|---|---|---|
| pTrcSCPHY | trc | Poly His | 18 | 150 | JM109 |
| pCalSCPHY | T7 | Calmodulin binding protein | 31 | 154 | BL21 (DE3) |
| pETSCPHY | T7 | Poly His | 32 | 154 | BL21 (DE3) |
| pGEXSCPHY | tac | Glutathione-S-tranferase | 224 | 177 | JM109 |
| pMALPHY | tac | Maltose Binding Protein | 390 | 193 | JM109 |

The "fusion tags" each comprised a member of a specific binding complex as a purification aid and to improve the solubility and stability of the expressed protein. These plasmids were transformed into the *E. coli* strains indicated in Table 2 and expression of the single-chain toxin was monitored.

In another experiment, the single-chain BoNT/A construct was inserted into plasmid pMAL-c2 between the Bam HI and Hind III restriction sites, resulting in a coding sequence for a fusion polypeptide containing the maltose binding protein at the N terminus, followed by a Factor Xa cleavage site. Transformant JM 109 colonies were selected in Luria broth containing ampicillin. Expression was induced by the addition of IPTG to a final concentration of 0.3 mM. As for the TeTx construct, aliquots of the cell culture were collected before and after induction, the cells in each sample lysed by sonication, and the supernatant prepared for SDS-PAGE under both reducing and non-reducing conditions. Following electrophoresis to separate the proteins according to apparent molecular weight, the gel was subjected to a Western blot using an antibody raised against the H chain of BoNT/A. The Western blot resulted in the appearance of an immunologically reactive single-chain toxin band of apparent molecular weight approximately 200 kDa. Further modifications of the single-chain BoNT molecule to eliminate fortuitous protease cleavage sites (similar to those modifications made at the TeTx site labile to trypsin and Arg C protease, described above) will result in even greater stability of the single-chain BoNT/A molecule.

Example 8

Construction of a Plasmid Vector Expressing BoNT/E

A plasmid expressing a single-chain recombinant version of the neurotoxin from *Clostridium botulinum* subtype E (strain Beluga) (BoNT/E) was constructed as follows. PCR primers were designed based on the EMBL database cDNA sequence of the BoNT/E neurotoxin (Genbank accession number X62089) This nucleotide sequence is represented herein as SEQ ID NO: 10.

```
gaattcaagt agtagataat aaaaataatg ccacagattt
ttattattaa taatgatata tttatctcta actgtttaac
tttaacttat aacaatgtaa atatatattt gtctataaaa
aatcaagatt acaattgggt tatatgtgat cttaatcatg
atataccaaa aaagtcatat ctatggatat taaaaaatat
ataaatttaa aattaggaga tgctgtatat gccaaaaatt
aatagtttta attataatga tcctgttaat gatagaacaa
ttttatatat taaaccaggc ggttgtcaag aattttataa
atcatttaat attatgaaaa atatttggat aattccagag
agaaatgtaa ttggtacaac cccccaagat tttcatccgc
ctacttcatt aaaaaatgga gatagtagtt attatgaccc
taattattta caaagtgatg aagaaaagga tagattttta
aaaatagtca caaaaatatt taatagaata aataataatc
tttcaggagg gattttatta gaagaactgt caaaagctaa
tccatattta gggaatgata atactccaga taatcaattc
catattggtg atgcatcagc agttgagatt aaattctcaa
atggtagcca agacatacta ttacctaatg ttattataat
gggagcagag cctgatttat ttgaaactaa cagttccaat
atttctctaa gaaataatta tatgccaagc aatcaccgtt
ttggatcaat agctatagta acattctcac ctgaatattc
ttttagattt aatgataatt gtatgaatga atttattcaa
gatcctgctc ttacattaat gcatgaatta atacattcat
tacatggact atatgggct aaagggatta ctacaaagta
tactataaca caaaaacaaa atcccctaat aacaaatata
agaggtacaa atattgaaga attcttaact tttggaggta
ctgatttaaa cattattact aaacttagca aagtacaagt
atctaatcca ctacttaatc cttataaaga tgtttttgaa
gcaaagtatg gattagataa agatgctagc ggaatttatt
cggtaaatat aaacaaattt aatgatattt ttaaaaaatt
atacagcttt acggaatttg atttacgaac taaatttcaa
gttaaatgta ggcaaactta tattggacag tataaatact
tcaaactttc aaacttgtta aatgattcta tttataatat
atcagaaggc tataatataa ataatttaaa ggtaaatttt
agaggacaga atgcaaattt aaatcctaga attattacac
caattacagg tagaggacta gtaaaaaaaa tcattagatt
ttgtaaaaat attgtttctg taaaaggcat aaggaaatca
atatgtatcg aaataaataa tggtgagtta tttttttgtgg
cttccgagaa tagttataat gatgataata taaatactcc
taaagaaatt gacgatacag taacttcaaa taataattat
gaaaatgatt tagatcaggt tattttaaat tttaatagtg
aatcagcacc tggactttca gatgaaaaat taaatttaac
tatccaaaat gatgcttata taccaaaata tgattctaat
ggaacaagtg atatagaaca acatgatgtt aatgaactta
atgtattttt ctatttagat gcacagaaag tgcccgaagg
tgaaaataat gtcaatctca cctcttcaat tgatacagca
ttattagaac aacctaaaat atatacattt ttttcatcag
aatttattaa taatgtcaat aaacctgtgc aagcagcatt
atttgtaagc tggatacaac aagtgttagt agattttact
actgaagcta accaaaaaag tactgttgat aaaattgcag
atatttctat agttgttcca tatataggtc ttgctttaaa
tataggaaat gaagcacaaa aaggaaattt taaagatgca
cttgaattat taggagcagg tatttttatta gaatttgaac
ccgagctttt aattcctaca attttagtat tcacgataaa
atcttttta ggttcatctg ataataaaaa taagttatt
aaagcaataa ataatgcatt gaaagaaaga gatgaaaaat
ggaagaagt atatagtttt atagtatcga attggatgac
taaaattaat acacaattta ataaaagaaa agaacaaatg
tatcaagctt tacaaaatca agtaaatgca attaaaacaa
taatagaatc taagtataat agttatactt tagaggaaaa
aaatgagctt acaaataaat atgatattaa gcaaatagaa
aatgaactta atcaaaaggt ttctatagca atgaataata
tagacaggtt cttaactgaa agttctatat cctatttaat
gaaaataata aatgaagtaa aaattaataa attaagagaa
tatgatgaga atgtcaaaac gtatttattg aattatatta
tacaacatgg atcaatcttg ggagagagtc agcaagaact
```

-continued

```
aaattctatg gtaactgata ccctaaataa tagtattcct tttaagcttt cttcttatac agatgataaa attttaattt catattttaa taaattcttt aagagaatta aaagtagttc agtttaaat atgagatata aaaatgataa atacgtagat acttcaggat atgattcaaa tataaatatt aatggagatg tatataaata tccaactaat aaaaatcaat ttggaatata taatgataaa cttagtgaag ttaatatatc tcaaaatgat tacattatat atgataataa atataaaaat tttagtatta gtttttgggt aagaattcct aactatgata ataagatagt aaatgttaat aatgaataca ctataataaa ttgtatgaga gataataatt caggatggaa agtatctctt aatcataatg aaataatttg gacattcgaa gattatataa ataagtggat ttttgtaact ataactaatg atagattagg agattctaaa ctttatatta atggaaattt aatagatcaa aaatcaattt taaatttagg taatattcat gttagtgaca atatatatt taaaatagtt aattgtagtt atacaagata tattggtatt agatatttta atatttttga taaagaatta gatgaaacag aaattcaaac tttatatagc aatgaaccta atacaaatat tttgaaggat ttttggggaa attatttgct ttatgacaaa gaatactatt tattaaatgt gttaaaacca aataacttta ttgataggag aaaagattct actttaagca ttaataatat aagaagcact attctttag ctaatagatt atatagtgga ataaaagtta aaatacaaag agttaataat agtagtacta acgataatct tgttagaaag aatgatcagg tatatattaa ttttgtagcc agcaaaactc acttatttcc attatatgct gatacagcta ccacaaataa agagaaaaca ataaaaatat catcatctgg caatagattt aatcaagtag tagttatgaa ttcagtagga aattgtacaa tgaattttaa aaataataat ggaaataata ttgggttgtt aggtttcaag gcagatactg tcgttgctag tacttggtat tatacacata tgagagatca tacaaacagc aatggatgtt tttggaactt tatttctgaa gaacatggat ggcaagaaaa ataaaaatta gattaaacgg ctaaagtcat aaattcc
```

The forward primer had the following nucleotide base sequence: CCCGGATCC CCA AAA ATT AAT AGT TTT AAT TAT AAT G SEQ ID NO: 11 where the BamHI endonuclease site is underlined and the sequence of the light chain minus the start codon is in bold.

The inverse primer had the sequence: CCCCTGCAG tca TTT TTC TTG CCA TCC ATG TTC TTC SEQ ID NO: 12 where the PstI endonuclease site is underlined, the end of the coding region of the heavy chain is in bold, and the stop codon is in lower case. These primers were made using standard DNA synthesis methodology.

The two primers were used in a PCR reaction containing different amounts of Clostridium botulinum type E (strain beluga) chromosomal DNA. The PCR reaction employed a DNA polymerase with proofreading activity (Pfx DNA polymerase, obtained from Life Technology) in order to avoid sequence errors in the amplified gene. The amplification reaction conditions were as follows: 30 cycles of: a 45 second denaturation at 95° C., followed by a 45 second annealing step at 56° C., followed by a primer extension reaction for 3 minutes 48 seconds at 68° C.

The PCR product was digested with BamHI and HindIII, and the digest subjected to agarose gel electrophoresis. Staining of the agarose gel with ethidium bromide revealed a major DNA fragment of approximately 3.5 kilobases (see FIG. 10). The band containing this fragment was excised from the gel, and the DNA purified from the agarose and ligated to BamHI and HindIII-cut pQE30 vector (Qiagen). The resulting ligated plasmid was used to transform E. coli strain JM 109 as described above, and the transformants plated onto selective LB agar plates. Several clones were recovered and the presence of the correct BoNT/E DNA insert checked by restriction digest. The resultant construct contains the BoNT/E gene (minus the first methionine) fused to the His$_6$ tag of the pQE30 vector, and contains 2 extra amino acid residues (glycine, serine), which are contributed by the engineered BamHI site.

Example 9

Construction of a Proteolytically-Inactive Mutant of BoNT/E by Site Directed Mutagenesis By mutating the glutamic acid at position 212 (within the active site) of the BoNT/E polypeptide construct to glutamine, a proteolytically-inactive and non-toxic single chain BoNT/E polypeptide was obtained.

The glutamine replacement was introduced on the forward primer using routine site directed mutagenesis methods. The mutagenic DNA primer had the sequence cag TTA ATA CAT TCA TTA CAT GGA CTA TAT G SEQ ID NO: 13 where the codon encoding glutamine at position 212 is indicated in small letters.

An inverse PCR reaction was performed using the above primer, along with the reverse primer ATG CAT TAA TGT AAG AGC AGG ATC TT SEQ ID NO: 14

And Pfx DNA polymerase (Life Technology) as above. The PCR template was the wild-type single-chain BoNT/E construct (termed pQEESCwt). The cycling parameters (30 cycles) were as follows: 1) a 45 second denaturation step at 95° C.; 2) a 45 second annealing step at 56° C.; and 3) a 7 minute 10 second extension step at 68° C.

Figure 11:
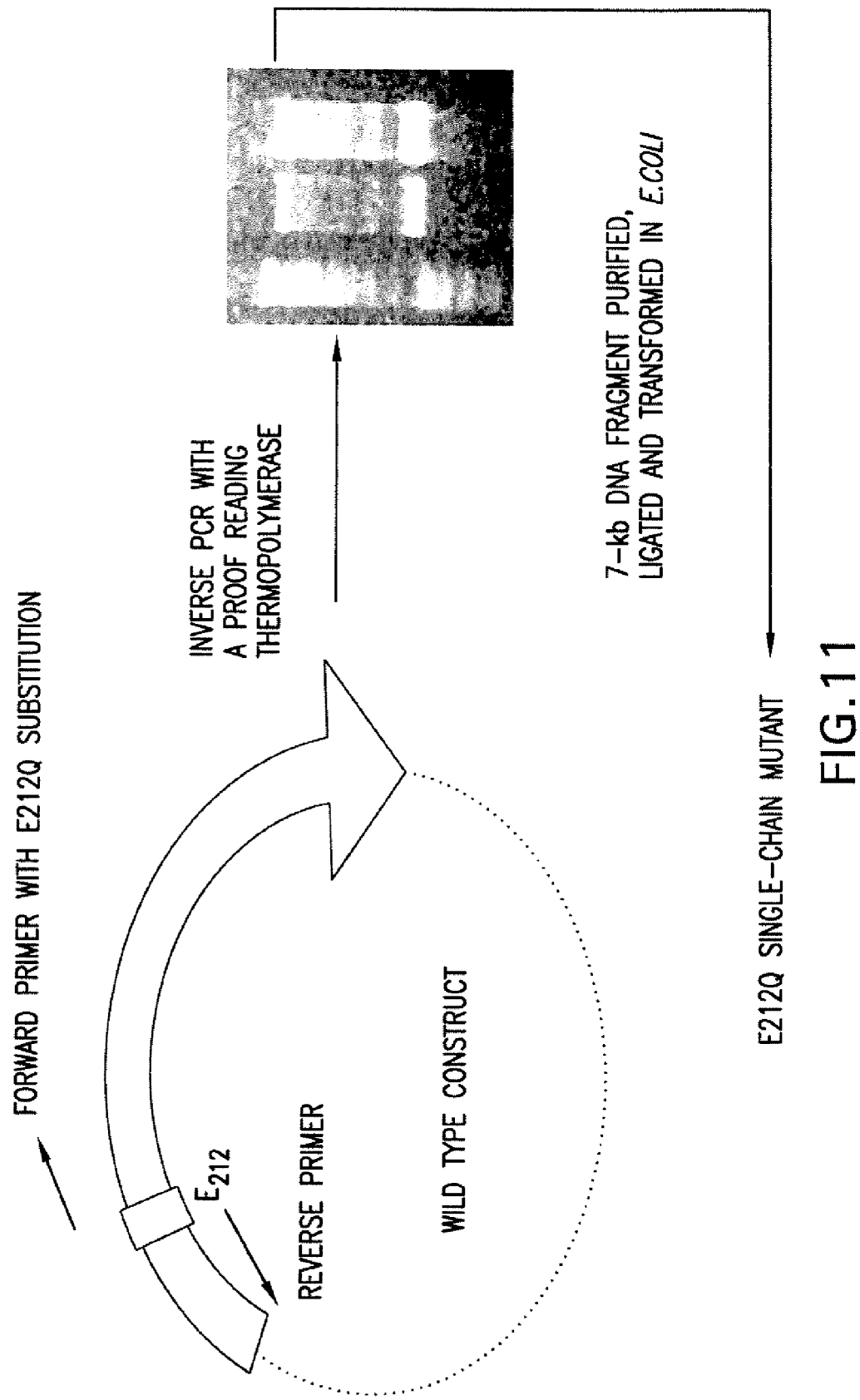
FIG. 11 shows the scheme for construction of a plasmid encoding the E212Q proteolytically inactive single-chain BoNT/E mutant, and an agarose gel electrophoretogram of the inverse PCR fragment obtained during the construction of the plasmid.

At the end of the amplification reaction, the DNA template was digested by the restriction enzyme Dpnl to permit selection of mutated clones only. After subjecting the PCR product to agarose gel electrophoresis, a band of approximately 7 kilobases was removed and the DNA purified and used for self-ligation in the presence of T4 DNA ligase (Promega) and polynucleotide kinase (Promega) to permit phosphorylation of the PCR product. The ligation mixture was used to transform E. coli strain DH10B, and the transformants plated onto selective agar plates. The presence of the correct plasmide construct was verified in several representative transformants by restriction digest and the mutation confirmed also by DNA sequencing. FIG. 11 shows the protocol for construction of the mutant BoNT/E plasmid, and an ethidium bromide-stained agarose gel of the PCR reaction mixture (lanes 2 and 3) versus molecular weight markers (lane 1).

Example 10

Purification of Single Chain Recombinant BoNT/E

The presence of the histidine tag at the N-terminus of the expressed protein allowed a single-step purification of the recombinant neurotoxin by metal-affinity chromatography.

The *E. coli* strain M15 (Qiagen) was used for expression of the BoNT/E single-chain construct. This strain carries an endogenous plasmid (pREP4, kanamycin resistant) containing a region encoding the lac $1^q$ repressor gene in order to prevent transcription of the neurotoxin gene prior to induction with IPTG. The pQE30 vector contains a T5 bacteriophage RNA polymerase promoter, which is also recognized by *E. coli* RNA polymerase.

A colony of M15 cells containing pQEESCwt was grown at 37° C. overnight in 5 ml of 2TY medium containing 0.1 mg/ml ampicillin; 0.025 mg/ml kanamycin and 0.2% glucose (w/v), and the resultant culture used to inoculate 500 ml of the same medium. When this second culture reached an optical density of 0.5-0.8 at 600 nm, IPTG was added to a final concentration of 0.3 mM and the culture incubated at 25° C. overnight to permit expression of the neurotoxin.

Subsequent centrifugation of the culture yielded ~2.3 g of wet cell pellet which was resuspended in 10 ml of extraction buffer (20 mM Hepes pH 7.0, 300 mM NaCl, 5 mM benzamidine, 2 µM pepstatin and 2 µM E-64). Lysozyme was added to a final concentration of 0.25 mg/ml, and the cell suspension incubated on ice for 60 minutes. Approximately 0.5 ml of glass beads (0.1 mm diameter from Biospec) was added to the cell suspension, followed by vortexing for 2 minutes to break the cells. Cell-free extracts was obtained by centrifugation at 10,000×g for 30 minutes at 4° C. The supernatant was incubated with 0.5 ml of TALON® cobalt metal affinity agarose resin (Clontech) pre-washed with extraction buffer in a rocking platform for 45 minutes at 4° C. The resin was then loaded into a disposable chromatography column and washed twice with 10 bed volumes of wash buffer (20 mM Hepes pH 7.0, 300 mM NaCl, 2 mM imidazole) before eluting the bound neurotoxin in 6 bed volumes of elution buffer (20 mM Hepes pH 7.0, 300 mM NaCl, 150 mM imidazole).

The elute was dialyzed overnight at 4° C. against 10 mM Hepes (pH 7.0) containing 150 mM NaCl and concentrated by centrifugal filtration (MW cutoff 10 KDa) to a final concentration of 1 mg/ml protein.

As shown in FIG. 12, the purity of the affinity-purified toxin was demonstrated by SDS-PAGE under reducing conditions, followed by Coomassie staining and Western-blotting, detecting the N-terminus with a mouse monoclonal anti-His antibody from Quiagen (diluted 2000 fold). Enhanced Chemiluminescence solutions (Santa Cruz) and mouse secondary horseradish peroxidase (affinity purified from Sigma) were used for detection of bound antibody. Approximately 2 µg of protein samples were loaded per well.

Example 11

Trypsin Activation of Purified Recombinant BoNT/E Single-Chain Polypeptide

Figure 13:
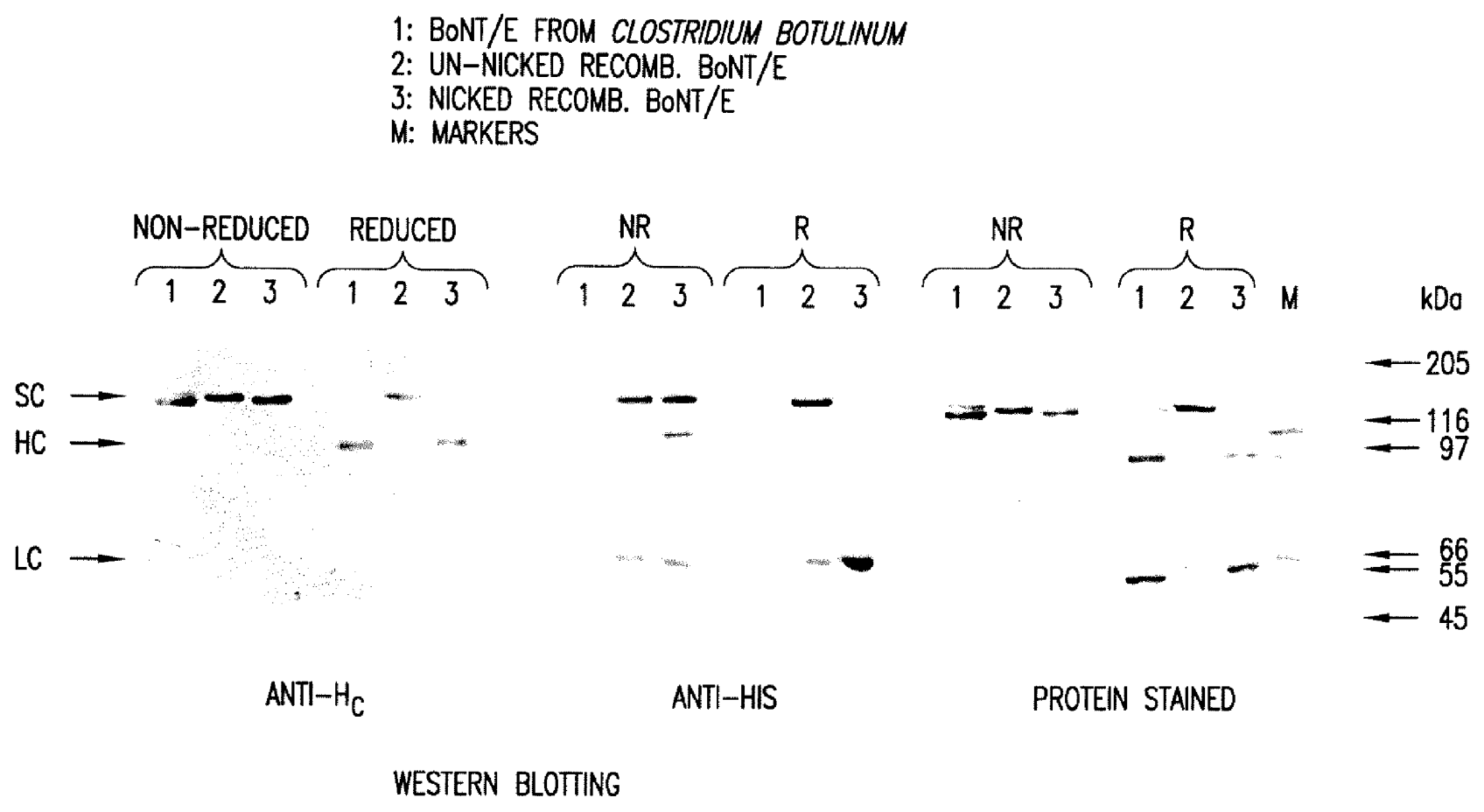

Purified BoNT/E single-chain neurotoxin polypeptide samples were activated by nicking the single chain with trypsin (1.5 µg/ml final concentration) for 60 minutes at a concentration of 1 mg toxin/ml in 10 mM Hepes (pH 7.0), 150 mM NaCl. Following the reaction, the trypsin was inactivated using 0.5 mM PMSF and 10 µg trypsin inhibitor/ml. The quality of the trypsinization was assessed and verified by SDS-PAGE under both reducing and non-reducing conditions, then staining with Coomassie staining and Western blotting the polyacrylamide gel using a mouse monoclonal anti-His antibody (Quiagen, diluted 2000-fold) and a mouse monoclonal anti-$H_C$ IgG (diluted 26-fold). As shown in FIG. 13, the Commassie-stained nicked protein resolves into two bands under reducing conditions, while the heavy and light chains remain disulfide-linked under non-reducing conditions, similar to the native toxin. The antibody-detected recombinant heavy chain is of approximately identical size as its wild-type *Clostridium* counterpart, whereas the recombinant light chain migrates at a slightly higher molecular weight compared to the native protein. This latter characteristic is due to the extra residues provided by the $His_6$ tag at the N-terminus.

Example 12

Recombinant BoNT/E is Proteolytically Active

Stock solutions (1 µM) of native nicked BoNT/E toxin, un-nicked single-chain recombinant toxin, nicked di-chain recombinant toxin, and nicked mutant (E212Q) BoNT/E were prepared in HEPES-buffered saline (HBS, 150 mM NaCl, 10 mM HEPES, pH 7.4, 10 µg/ml BSA). These samples were incubated for 30 minutes at 37° C. in the absence or presence of 20 mM DTT, and then serially diluted in 0.02 ml of HBS to the final concentrations shown in FIG. 14.

A recombinant peptide containing amino acids 140-205 of SNAP-25 fused to glutathione-S-transferase (termed GST-SNAP-25 [140-205]) was used as a protease substrate to test the proteolytic activity of the recombinant BoNT/E polypeptides. Ten micrograms this protease substrate was incubated with the toxin samples. The digestion reaction was allowed to proceed for 30 minutes at 37° C. in the absence or presence of 2 mM DTT, and stopped by addition of SDS-PAGE sample buffer followed by boiling for 5 minutes.

Figure 14:
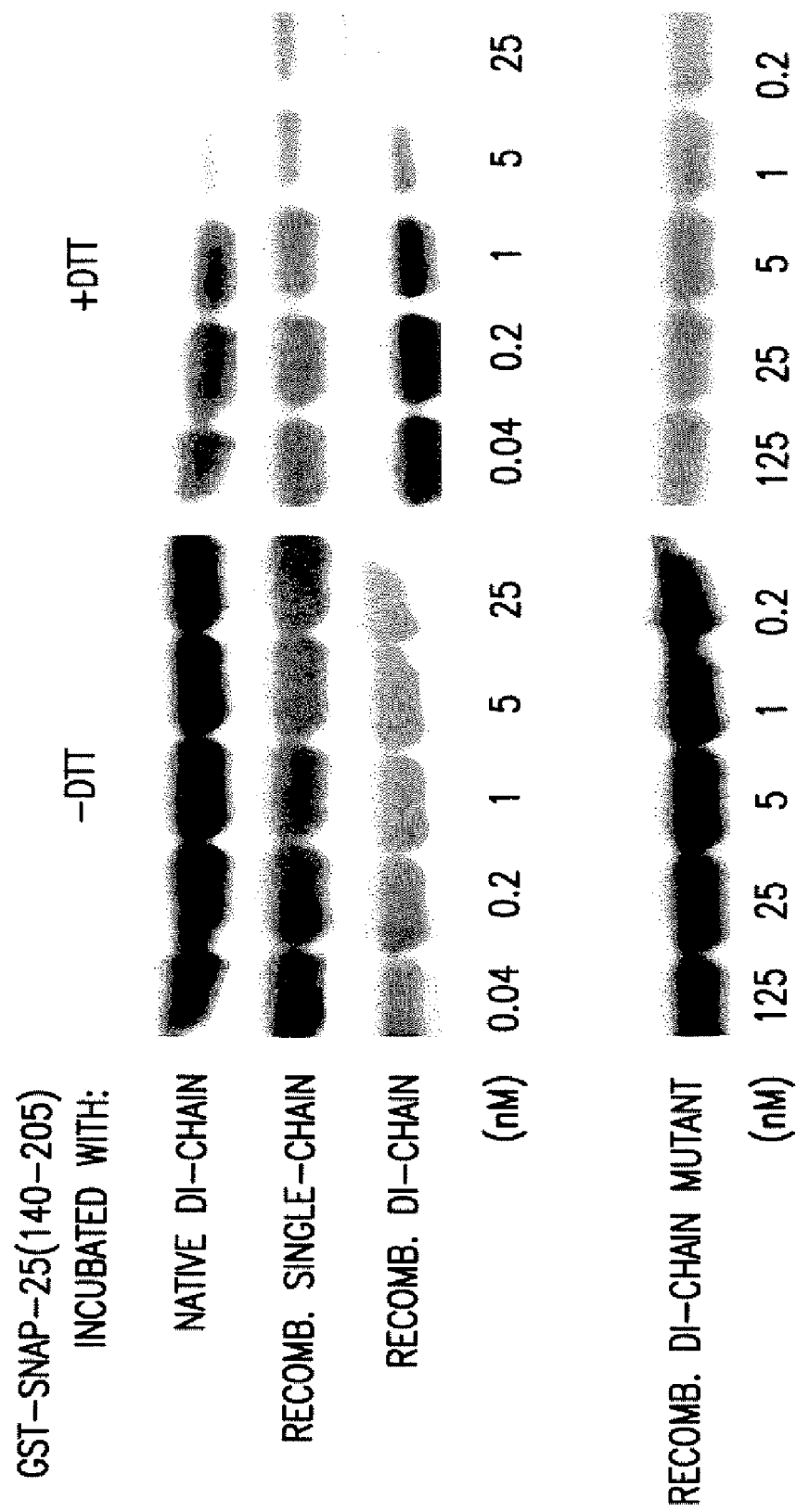
FIG. 14 shows the results of incubating native BoNT/E, recombinant nicked and un-nicked BoNT/E, and the E212Q mutant with a GST-SNAP-25[140-205] protease substrate.

The resultant samples were analyzed by SDS-PAGE (3 µg of GST-SNAP-25 [140-205] per lane) and silver staining. As FIG. 14 demonstrates, even unnicked recombinant single chain toxin retains proteolytic activity. As expected, the mutant E212Q BoNT/E construct has no detectable proteolytic activity. FIG. 14 shows only the GST-SNAP-25-[140-205] bands.

Example 13

Nicking Makes Recombinant BoNT/E Fully Functional

Cerebellar neurons maintained for 10 days in culture ($2\times10^6$/22 mm diameter well) were washed with Krebs-Ringer HEPES (KRH) buffer, then exposed to the specified concentrations of BoNT/E native (●), trypsin-nicked recombinant (○), or un-nicked single-chain (▼) BoNT/E. (See FIG. 15). After 60 minutes at 37° C., the toxin-containing buffer was removed and the cells were washed twice, then incubated with KRH buffer containing 0.25 µCi/ml [$^{14}$C]-labeled glutamine (i.e. the glutamate precursor). After 45 minutes, the latter medium was removed and the neurons were washed four times at 37° C. prior to assessment of transmitter glutamate release. Control and toxin-treated neurons were incubated for 5 minutes at 37° C. in KRH buffer containing either 1.4 mM $Ca^{2+}$ or 0.5 mM EGTA to assess $Ca^{2+}$-independent release; aliquots were then removed for determination of their [$^{14}$C]-glutamate content (see below).

Immediately after removal of the basal medium, KRH buffer containing 50 mM KCl and either 1.4 mM $Ca^{2+}$ or 0.5 mM EGTA was added; as before, aliquots were removed for [$^{14}$C]-glutamate assay after a 5 minute stimulation period. Finally, neurons were solubilized with 20 mM EGTA.NaOH pH 7.5 containing 1% (w/v) SDS and aliquots were removed to determine the amounts of radioactivity remaining within the cells. The amount of [$^{14}$C]-glutamate in each of the samples was assayed by scintillation counting and the levels released under basal and stimulated conditions were expressed as percentages relative to the calculated total cell content.

The percent [$^{14}$C]-glutamate content in the EGTA-containing buffer for each sample was subtracted from the values recorded in $Ca^{2+}$-containing KRH samples in order to obtain the $Ca^{2+}$-dependent component of release, and the latter basal readings were subtracted from values obtained for 50 mM KCl samples to yield $K^+$-evoked $Ca^{2+}$-dependent release. The values, thus, obtained from toxin-treated neurons are expressed relative to toxin-free controls.

Figure 15:
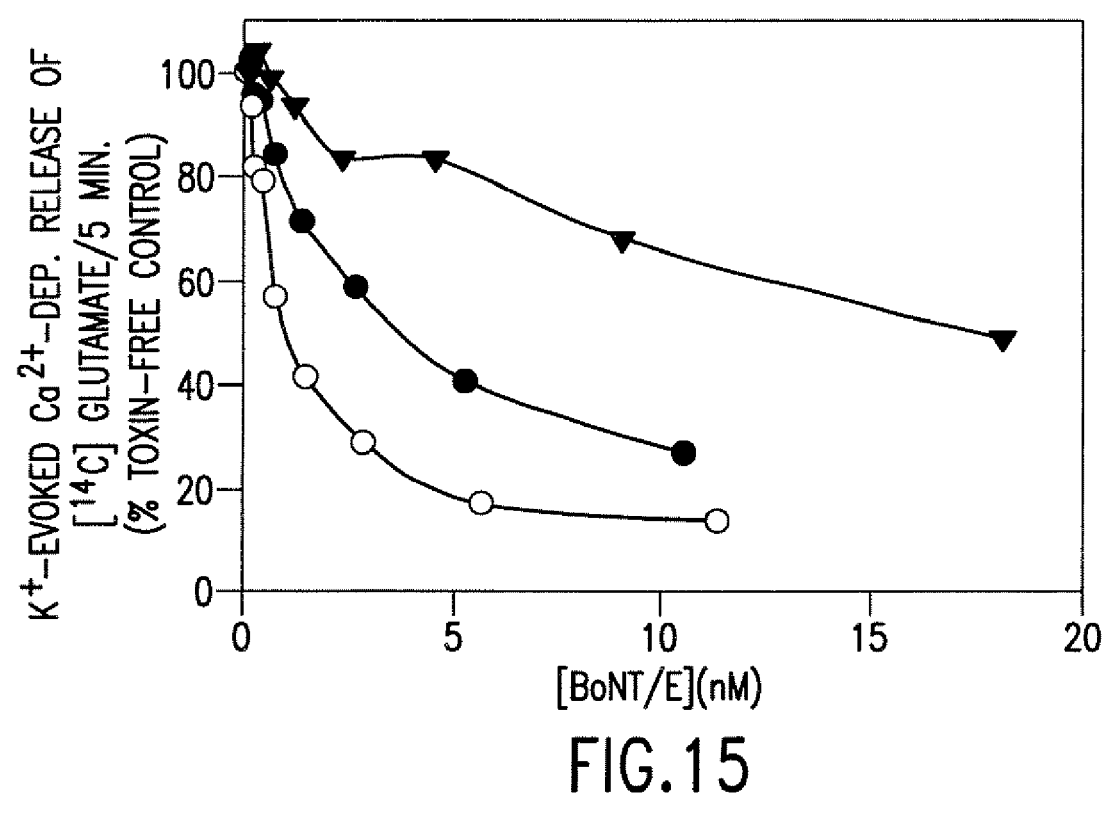

FIG. 15 shows that, despite retaining proteolytic activity, the un-nicked recombinant BoNT/E has markedly less activity than either the native BoNT/E or the nicked recombinant version. This finding may reflect the inability of the un-nicked toxin to adequately enter the target cell. Additionally, the nicked recombinant version appears to be more effective in inhibiting glutamate release than the native toxin.

Example 14

Figure 16A:
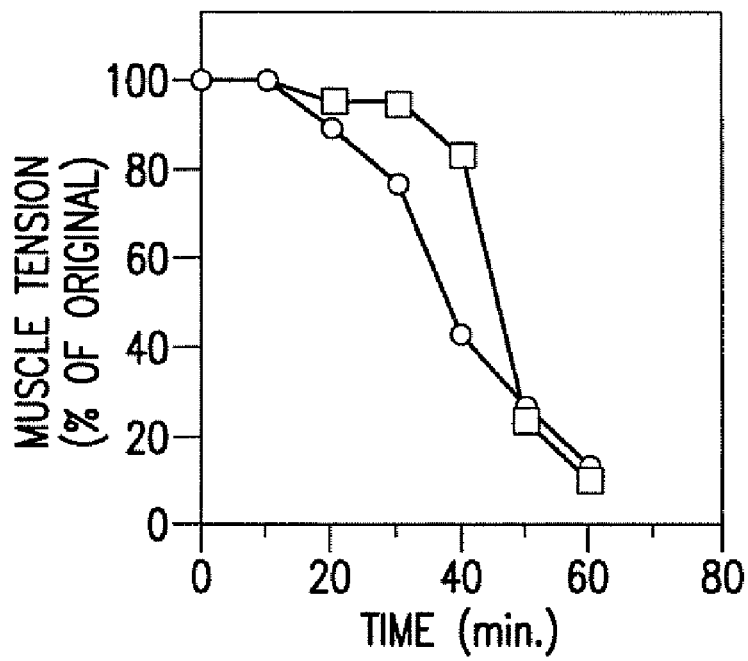
FIG. 16A shows the effects on muscle tension of incubating mouse phrenic-nerve hemi-diaphragms with 0.2 nM recombinant nicked BoNT/E (○) or 0.2 nM native BoNT/E (□).
Figure 16B:
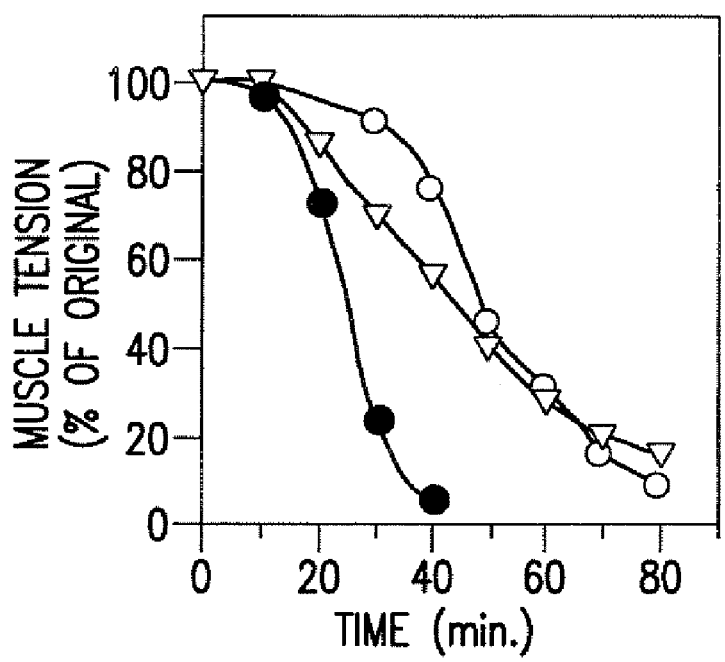
FIG. 16B shows the effects on muscle tension of incubating mouse phrenic-nerve hemi-diaphragms with 1 nM recombinant un-nicked (○), 1 nM recombinant nicked (●) or 0.05 nM recombinant nicked (∇) BoNT/E.

Recombinant BoNT/E has a Neuromuscular Paralytic Activity Equivalent to that of the Native Toxin at Mouse Neuromuscular Endplates: Nicking Increases Potency Mouse phrenic-nerve hemi-diaphragms were bathed in KR supplemented with 0.1% BSA and saturated with 95% $O_2$/5% $CO_2$. The phrenic nerves were stimulated (0.2 Hz, 1.5-2.5 mV) and nerve evoked muscle tension was recorded before and after the addition of (FIG. 16A) 0.2 nM recombinant nicked BoNT/E (○) or 0.2 nM native BoNT/E (□), and (FIG. 16B) 1 nM recombinant un-nicked (○), 1 nM recombinant nicked (●) or 0.05 nM recombinant nicked (∇) BoNT/E. As shown in FIGS. 16A and 16B, the recombinant nicked BoNT/E is an effective paralytic agent, displaying greater activity in this assay that the native toxin. The un-nicked toxin displays significantly lower activity than the nicked toxin in this assay.

The neuromuscular paralytic activity of recombinant nicked BoNT/E was also demonstrated in mice by intramuscular injection into hind-limb muscles. This resulted in paralysis, as assessed by the toe spread reflex assay, with a pattern of symptoms typical of botulism.

The in vivo neurotoxicity of the nicked, recombinant neurotoxin was established, by injecting the toxin into mice, to have a specific neurotoxicity of less than $10^7$ mouse $LD_{50}$ units per mg.

Example 15

Figure 17:
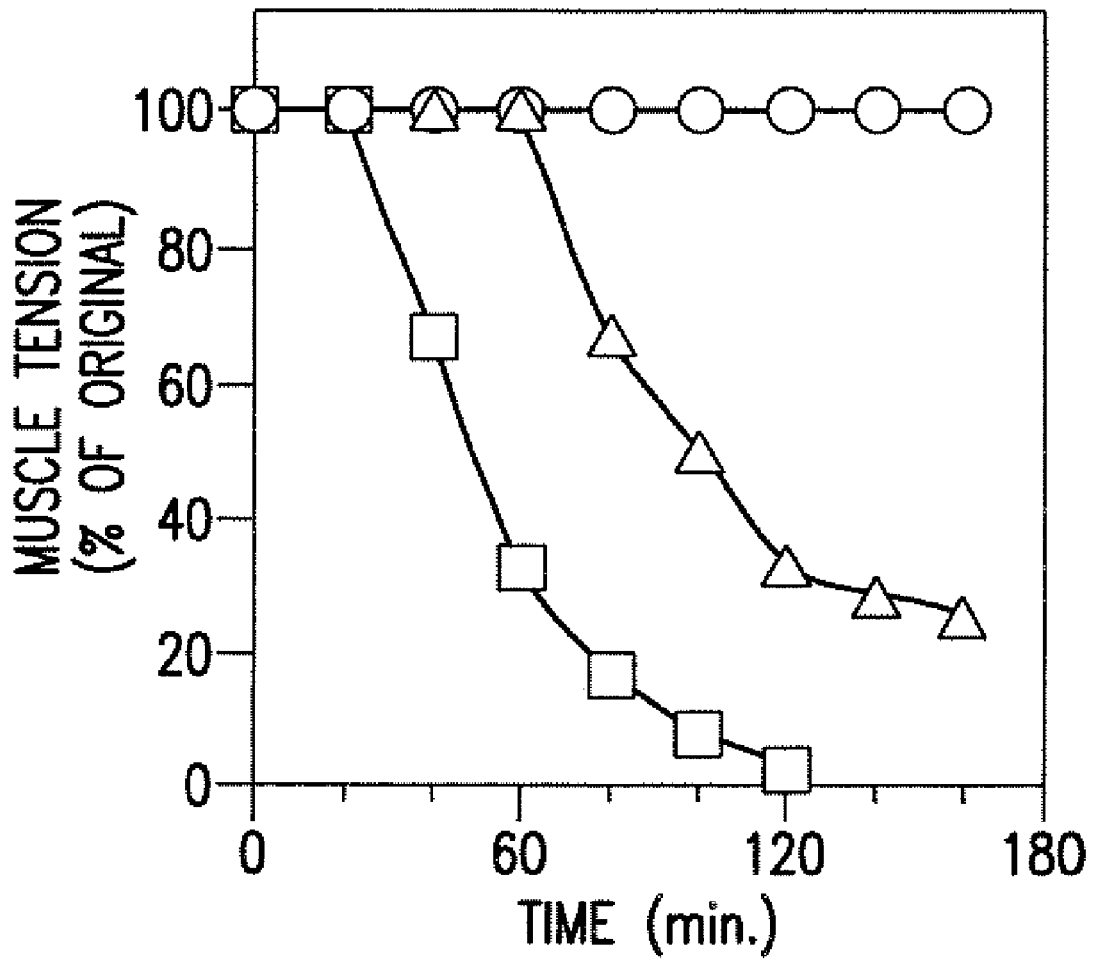
FIG. 17 shows the attenuation of paralytic activity on mouse phrenic-nerve hemi-diaphragms of preincubation with the inactive E212Q mutant prior to exposure to native nicked BoNT/E toxin.

The BoNT/E E212Q Protease Inactive Mutant Antagonises BoNT/E-Induced Neuroparalysis A mouse phrenic-nerve hemi-diaphragm was exposed to 10 nM BoNT/E E212Q in KR medium, the nerve was stimulated and evoked muscle tension was recorded. As indicated by FIG. 17, the BoNT E212Q mutant does not inhibit neurotransmission, as determined by its failure to reduce nerve-evoked muscle tension (○). To assess the ability of this non-toxic mutant to antagonise the activity of the native toxin, mouse phrenic-nerve hemi-diaphragms were bathed for 60 minutes at 4° C. in MKR supplemented with 0.1% BSA and saturated with 95% $O_2$/5% $CO_2$, without (□) or with (Λ) the inclusion of 5 nM BoNT/E E212Q. Native nicked BoNT/E was added to each bath (0.05 nM final) and the tissues were incubated for a further 30 min. The nerve-muscles were then washed three times each with MKR followed by KR, before the temperature was raised to 37° C., the nerve stimulated and evoked muscle tension recorded.

As shown in FIG. 17, the onset of native BoNT/E activity in this assay was delayed and antagonized when the phrenic-nerve hemi-diaphragms are preincubated with the E212Q protease inactive mutant, thereby indicating that the recombinant mutant faithfully binds to the same cell surface receptor as does the native toxin. Thus, the methods of the present patent application can be used to produce recombinant and modified toxins having fully functional receptor binding domains, and BoNT-related transported molecules for the intracellular delivery of therapeutic agents.

Those of skill in the art will understand that the Examples provided herein describe preferred compositions and methods, and that a variety of different cloning strategies, protease cleavage sites, and specific binding complex members may be employed in the practice and use of the present invention while remaining within the invention's scope. Additionally, different dichain or binary toxin molecules and modified versions thereof (for example, BoNT/B-E and modified variants thereof) may be used as the basis for the methods and compositions of the present invention.

What is claimed is:

1. A cleavable single-chain polypeptide comprising:
   a) a first amino acid sequence region comprising
      i) a first domain comprising a BoNT/A neurotoxin heavy chain binding element able to preferentially interact with a target cell surface marker under physiological conditions; and
      ii) a second domain comprising a BoNT/A neurotoxin heavy chain translocation element able to facilitate the transfer of said single-chain polypeptide across a vesicular membrane; and
   b) a second amino acid sequence region comprising a BoNT/A neurotoxin light chain or a portion thereof retaining a SNARE-protein sequence-specific endopeptidase activity;
   c) a third amino acid sequence region comprising a non-native Clostridial neurotoxin protease cleavage site;
   wherein said first and second amino acid sequence regions are separated by said third amino acid sequence region.

2. The polypeptide of claim 1, wherein said protease cleavage site is cleaved by a tobacco etch virus protease, a human rhinovirus 3C protease, or a bovine enterokinase.

3. The polypeptide of claim 1, wherein said protease cleavage site is cleaved by a non-human enterokinase, a protease from *Bacillus subtilus*, a protease from *Bacillus amyliquifaciens*, or a protease from a rhinovirus.

4. The polypeptide of claim 1, wherein the protease cleavage site comprises SEQ ID NO: 15, SEQ ID NO: 16, SEQ ID NO: 22 or SEQ ID NO: 23.

5. The polypeptide of claim 1, wherein said polypeptide comprises a fourth amino acid sequence region comprising a target-binding portion of a binding tag.

6. The polypeptide of claim 5, wherein said target-binding portion comprises a His$_6$, a monoclonal antibody, a maltose binding protein, a glutathione-S-transferase, a protein A or a calmodulin binding protein.

7. A nucleic acid molecule comprising an open reading frame encoding a cleavable single-chain polypeptide according to claim 5.

8. A method of making a cleavable single-chain polypeptide comprising:

a) inserting a nucleic acid molecule as defined by claim 7 into a suitable host cell, b) growing the host cell in culture, and c) permitting or inducing said host cell to express the single chain polypeptide encoded by the nucleic acid molecule.

9. A method of purifying a cleavable single chain polypeptide comprising:

a) lysing a host cell expressing a single chain polypeptide from a nucleic acid molecule as defined by claim 7 to produce a cell lysate;

b) contacting the cell lysate with a target compound so as to form a specific binding complex capable of being immobilized comprising the binding tag and the target compound; and c) separating the binding complex from the cell lysate.

10. A composition comprising an active di-chain form of the cleavable single-chain polypeptide defined in claim 1.

11. A nucleic acid molecule comprising an open reading frame encoding a cleavable single-chain polypeptide according to claim 1.

12. A method of making a cleavable single-chain polypeptide comprising:

a) inserting a nucleic acid molecule as defined by claim 11 into a suitable host cell, b) growing the host cell in culture, and c) permitting or inducing said host cell to express the single chain polypeptide encoded by the nucleic acid molecule.

* * * * *

UNITED STATES PATENT AND TRADEMARK OFFICE
CERTIFICATE OF CORRECTION

| | | |
|---|---|---|
| PATENT NO. | : 7,959,933 B2 | Page 1 of 3 |
| APPLICATION NO. | : 12/182801 | |
| DATED | : June 14, 2011 | |
| INVENTOR(S) | : J. Oliver Dolly et al. | |

It is certified that error appears in the above-identified patent and that said Letters Patent is hereby corrected as shown below:

On Title page 2, Item (56) in column 1, under "Other Publications", line 9, delete "CI" and insert -- C1--, therefor.

On Title page 2, Item (56) in column 1, under "Other Publications", line 18, delete "Neurotoxiicity" and insert -- Neurotoxicity --, therefor.

On Title page 2, Item (56) in column 2, under "Other Publications", line 2, delete "Cahins" and insert -- Chains --, therefor.

On Title page 2, Item (56) in column 2, under "Other Publications", line 8, delete "Proetin" and insert -- Protein --, therefor.

On Title page 2, Item (56) in column 2, under "Other Publications", line 15, delete "interation" and insert -- interaction --, therefor.

In column 1, line 11, after "1999," insert -- both of --.

In column 2, line 59, delete "bephlarospasm" and insert -- blepharospasm --, therefor.

In column 3, line 14, delete "disufide" and insert -- disulfide --, therefor.

In column 3, line 57, delete "BONT;" and insert -- BoNT; --, therefor.

In column 5, line 16, delete "chromotography" and insert -- chromatography --, therefor.

In column 5, line 42, delete "amyliquifaciens," and insert -- amyloliquefaciens, --, therefor.

In column 6, line 6-7, delete "tranporters," and insert -- transporters, --, therefor.

Signed and Sealed this
Tenth Day of January, 2012

David J. Kappos
*Director of the United States Patent and Trademark Office*

CERTIFICATE OF CORRECTION (continued)

U.S. Pat. No. 7,959,933 B2

In column 6, line 48, after "and" delete "a".

In column 7, line 25, after "the" delete "and".

In column 7, line 40, delete "Commassie" and insert -- Coomassie --, therefor.

In column 8, line 4, delete "diaphrams" and insert -- diaphragms --, therefor.

In column 8, line 17, delete "Westerm" and insert -- Western --, therefor.

In column 9, line 62-63, delete "zeamatus" and insert -- zeamais --, therefor.

In column 9, line 63, delete "crustacian" and insert -- crustacean --, therefor.

In column 9, line 66, delete "amyliquifaciens," and insert -- amyloliquefaciens, --, therefor.

In column 11, line 42, delete "TeNT," and insert -- TeTx, --, therefor.

In column 14, line 39, delete "excission" and insert -- excision --, therefor.

In column 14, line 42-43, delete " pMAL-LC-Ala$^2$," and insert -- pMAL-LC-Ala$^{234}$, --, therefor.

In column 15, line 23, delete "commecially" and insert -- commercially --, therefor.

In column 17, line 66, before "The" delete "a)"

In column 19, line 5, after "yielded" delete "a".

In column 19, line 32, delete "typsin" and insert -- trypsin --, therefor.

In column 21, line 9, delete "nickedf" and insert -- nicked --, therefor.

In column 21, line 27, delete "0.01$^1$" and insert -- 0.01$^d$ --, therefor.

In column 21, line 36, delete "v" and insert -- v° --, therefor.

In column 22, line 7, delete "tranferase" and insert -- transferase --, therefor.

In column 24, line 1, after "cattattact"
insert -- agtgctcagt ccaatgatat ctatactaat cttctagctg attataaaaa aatagcgtct --.

In column 25, line 20, after "gacattcgaa"
insert -- gataatcgag gaattaatca aaaattagca tttaactatg gtaacgcaaa tggtatttct --.

In column 26, line 45, delete "14" and insert -- 14. --, therefor.

CERTIFICATE OF CORRECTION (continued)
U.S. Pat. No. 7,959,933 B2

In column 27, line 50, delete "Quiagen" and insert -- Qiagen --, therefor.

In column 28, line 4, delete "Quiagen" and insert -- Qiagen --, therefor.

In column 28, line 6, delete "Commassie" and insert -- Coomassie --, therefor.

In column 44, line 53, in claim 3, delete "subtilus," and insert -- subtilis, --, therefor.

In column 44, line 53-54, in claim 3, delete "amyliquifaciens," and insert -- amyloliquefaciens, --, therefor.